(12) United States Patent
Balachandran et al.

(10) Patent No.: US 10,716,672 B2
(45) Date of Patent: Jul. 21, 2020

(54) SYSTEM AND METHOD FOR INTRAPROCEDURAL ASSESSMENT OF GEOMETRY AND COMPLIANCE OF VALVE ANNULUS FOR TRANS-CATHETER VALVE IMPLANTATION

(71) Applicant: St. Jude Medical, Cardiology Division, Inc., St. Paul, MN (US)

(72) Inventors: Ram Kumar Balachandran, Maple Grove, MN (US); Neelakantan Saikrishnan, Plymouth, MN (US); John Hauck, Shoreview, MN (US); Riki Thao, Little Canada, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 309 days.

(21) Appl. No.: 15/088,224

(22) Filed: Apr. 1, 2016

(65) Prior Publication Data

US 2016/0296333 A1 Oct. 13, 2016

Related U.S. Application Data

(60) Provisional application No. 62/143,968, filed on Apr. 7, 2015.

(51) Int. Cl.
*A61F 2/24* (2006.01)
*A61B 5/107* (2006.01)
(Continued)

(52) U.S. Cl.
CPC .......... *A61F 2/2496* (2013.01); *A61B 5/1076* (2013.01); *A61B 5/6853* (2013.01);
(Continued)

(58) Field of Classification Search
CPC .......... A61F 2/2496; A61F 2250/0045; A61B 5/1076; A61B 2018/00214;
(Continued)

(56) References Cited

U.S. PATENT DOCUMENTS 3,657,744 A 4/1972 Ersek
4,275,469 A 6/1981 Gabbay
(Continued)

FOREIGN PATENT DOCUMENTS

DE 19857887 A1 7/2000
DE 10121210 A1 11/2002
(Continued)

OTHER PUBLICATIONS

International Search Report and Written Opinion for Application No. PCT/US2016/025469 dated Jun. 16, 2016.
(Continued)

*Primary Examiner* — Sean P Dougherty
(74) *Attorney, Agent, or Firm* — Lerner, David, Littenberg, Krumholz & Mentlik, LLP

(57) ABSTRACT

A system for determining the dimensions of a native valve annulus may include a sensing catheter, a transmitter, and a computing device. The sensing catheter may include a shaft extending in a longitudinal direction; a plurality of splines attached to the shaft, the splines having an expanded condition spaced radially outward from the shaft; and at least one sensing coil located on each of the splines. The transmitter may generate a magnetic field to induce a potential in each of the sensing coils, and the computing device may identify the positions of the sensing coils based on the induced potentials.

14 Claims, 20 Drawing Sheets

(51) Int. Cl.
*A61B 5/00* (2006.01)
*A61B 17/00* (2006.01)
*A61B 18/00* (2006.01)

(52) U.S. Cl.
CPC ............ *A61B 2017/00243* (2013.01); *A61B 2018/0022* (2013.01); *A61B 2018/00214* (2013.01); *A61F 2250/0045* (2013.01)

(58) Field of Classification Search
CPC .. A61B 2017/00243; A61B 2018/0022; A61B 5/6853
See application file for complete search history.

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,480,423 A | 1/1996 | Ravenscroft et al. | |
| 5,553,611 A | 9/1996 | Budd et al. | |
| 5,662,108 A | 9/1997 | Budd et al. | |
| 5,843,167 A | 12/1998 | Dwyer et al. | |
| 5,855,601 A | 1/1999 | Bessler et al. | |
| 5,865,801 A * | 2/1999 | Houser | A61B 5/036 600/488 |
| 5,908,448 A * | 6/1999 | Roberts | A61F 2/958 606/194 |
| 5,935,163 A | 8/1999 | Gabbay | |
| 5,961,513 A | 10/1999 | Swanson et al. | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,498,944 B1 * | 12/2002 | Ben-Haim | A61B 5/0215 600/407 |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,690,963 B2 * | 2/2004 | Ben-Haim | A61N 1/36564 600/117 |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 6,939,309 B1 | 9/2005 | Beatty et al. | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,195,612 B2 * | 3/2007 | van Sloten | A61M 25/0009 604/103.1 |
| 7,247,167 B2 | 7/2007 | Gabbay | |
| 7,263,397 B2 | 8/2007 | Hauck et al. | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,386,339 B2 * | 6/2008 | Strommer | A61B 5/0066 600/424 |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,604,605 B2 * | 10/2009 | Zvuloni | A61B 5/02007 600/424 |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,856,730 B2 * | 12/2010 | Sakai | A61B 5/1076 33/542 |
| 7,914,569 B2 | 3/2011 | Nguyen et al. | |
| 7,951,111 B2 * | 5/2011 | Drasler | A61M 25/1002 604/100.01 |
| 7,963,929 B2 * | 6/2011 | Kassab | A61B 5/1076 600/561 |
| 8,012,149 B2 * | 9/2011 | Jackson | A61M 25/10184 606/32 |
| D648,854 S | 11/2011 | Braido | |
| 8,057,396 B2 * | 11/2011 | Forster | A61B 5/0536 600/437 |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| 8,298,161 B2 * | 10/2012 | Vargas | A61M 25/00 600/587 |
| 8,637,132 B2 * | 1/2014 | Bavaro | A61B 5/1076 428/36.9 |
| 8,728,012 B2 * | 5/2014 | Braido | A61B 5/02007 33/512 |
| 8,784,338 B2 * | 7/2014 | Wallace | A61B 5/053 600/587 |
| 8,827,929 B2 * | 9/2014 | O'Dea | A61B 5/037 600/485 |
| 8,840,558 B2 * | 9/2014 | Burns | A61B 5/6817 600/459 |
| 8,998,827 B2 * | 4/2015 | Drasler | A61M 29/02 600/587 |
| 9,107,749 B2 * | 8/2015 | Bobo | A61F 2/2445 |
| 9,119,564 B2 * | 9/2015 | Plassman | A61B 5/1076 |
| 9,492,113 B2 * | 11/2016 | Nagale | A61B 5/205 |
| 9,603,545 B2 * | 3/2017 | Kassab | A61B 5/053 |
| 9,808,179 B2 * | 11/2017 | O'Dea | A61B 5/0084 |
| 9,867,556 B2 * | 1/2018 | Balachandran | A61B 5/1076 |
| 2002/0036220 A1 | 3/2002 | Gabbay | |
| 2002/0087208 A1 * | 7/2002 | Koblish | A61B 18/1492 607/113 |
| 2003/0023303 A1 | 1/2003 | Palmaz et al. | |
| 2003/0050694 A1 | 3/2003 | Yang et al. | |
| 2003/0120318 A1 | 6/2003 | Hauck | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2004/0249267 A1 * | 12/2004 | Gilboa | A61B 1/00154 600/424 |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0251032 A1 * | 11/2005 | Smith | A61B 5/055 600/433 |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |

(56) References Cited

U.S. PATENT DOCUMENTS

| | | |
|---|---|---|
| 2006/0149360 A1 | 7/2006 | Schwammenthal et al. |
| 2006/0173300 A1* | 8/2006 | Oslund ............... A61B 5/1076 600/435 |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0156068 A1* | 7/2007 | Dubey ................ A61B 5/1076 600/588 |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0221643 A1 | 9/2008 | Olson |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0005674 A1 | 1/2009 | Saadat et al. |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0094328 A1 | 4/2010 | O'dea et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0210939 A1* | 8/2010 | Hartmann ............... A61B 5/062 600/424 |
| 2010/0217382 A1 | 8/2010 | Chau et al. |
| 2010/0228192 A1 | 9/2010 | O'Dea et al. |
| 2010/0228202 A1 | 9/2010 | O'Dea et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2010/0312181 A1 | 12/2010 | O'Dea |
| 2011/0029072 A1 | 2/2011 | Gabbay |
| 2011/0054395 A1 | 3/2011 | O'Dea et al. |
| 2012/0035642 A1 | 2/2012 | O'dea et al. |
| 2012/0065585 A1 | 3/2012 | O'Dea |
| 2012/0149968 A1* | 6/2012 | Brighton ................ A61N 1/326 600/13 |
| 2012/0277525 A1 | 11/2012 | O'Dea |
| 2013/0123694 A1 | 5/2013 | Subramaniyan et al. |
| 2014/0330133 A1* | 11/2014 | Stern .................... A61B 5/1076 600/479 |
| 2015/0223729 A1* | 8/2015 | Balachandran ...... A61B 5/1076 600/374 |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| EP | 2476453 A1 | 7/2012 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2005107841 A2 | 11/2005 |
| WO | 06073626 A2 | 7/2006 |
| WO | 2006090351 A1 | 8/2006 |
| WO | 07071436 A2 | 6/2007 |
| WO | 08070797 A2 | 6/2008 |
| WO | 2009001325 A1 | 12/2008 |
| WO | 2009001326 A1 | 12/2008 |
| WO | 2009001327 A2 | 12/2008 |
| WO | 2009001328 A2 | 12/2008 |
| WO | 2009081387 A1 | 7/2009 |
| WO | 2009125380 A1 | 10/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2010103501 A1 | 9/2010 |
| WO | 2010103502 A2 | 9/2010 |
| WO | 2011042893 A1 | 4/2011 |
| WO | 2011117852 A1 | 9/2011 |
| WO | 2012064623 A1 | 5/2012 |
| WO | 2012092016 A1 | 7/2012 |

OTHER PUBLICATIONS

Andersen, H. R. et al, Transluminal implantation of artificial heart valves, European Heart Journal (1992) 13, 704-708.

Andersen, Henning Rud, Transluminal Catheter Implanted Prosthetic Heart Valves, International Journal of Angiology 7:102-106 (1998).

Extended European Search Report for Application No. 15154142.2 dated Jun. 8, 2015.

Knudsen, L.L. et al., Catheter-implanted prosthetic heart valves, The International Journal of Artificial Organs, vol. 16, No. 5 1993, pp. 253-262.

Quaden, René et al., "Percutaneous aortic valve replacement: resection before implantation," 836-840, European J. of Cardio-thoracic Surgery 27 (2005).

Ruiz, Carlos, "Overview of PRE-CE Mark Transcatheter Aortic Valve Technologies", Euro PCR, May 25, 2010.

Transluminal Aortic Valve Placement, Moazami, Nader, et al., ASAIO Journal, 1996; 42:M381-M385.

U.S. Appl. No. 29/375,243, filed Sep. 20, 2010.

U.S. Appl. No. 29/375,260, filed Sep. 20, 2010.

(56) References Cited

OTHER PUBLICATIONS

Zegdi, Rachid, MD, PhD et al., "Is It Reasonable to Treat All Calcified Stenotic Aortic Valves With a Valved Stent?" 579-584, J. of the American College of Cardiology, vol. 51, No. 5, Feb. 5, 2008.

* cited by examiner

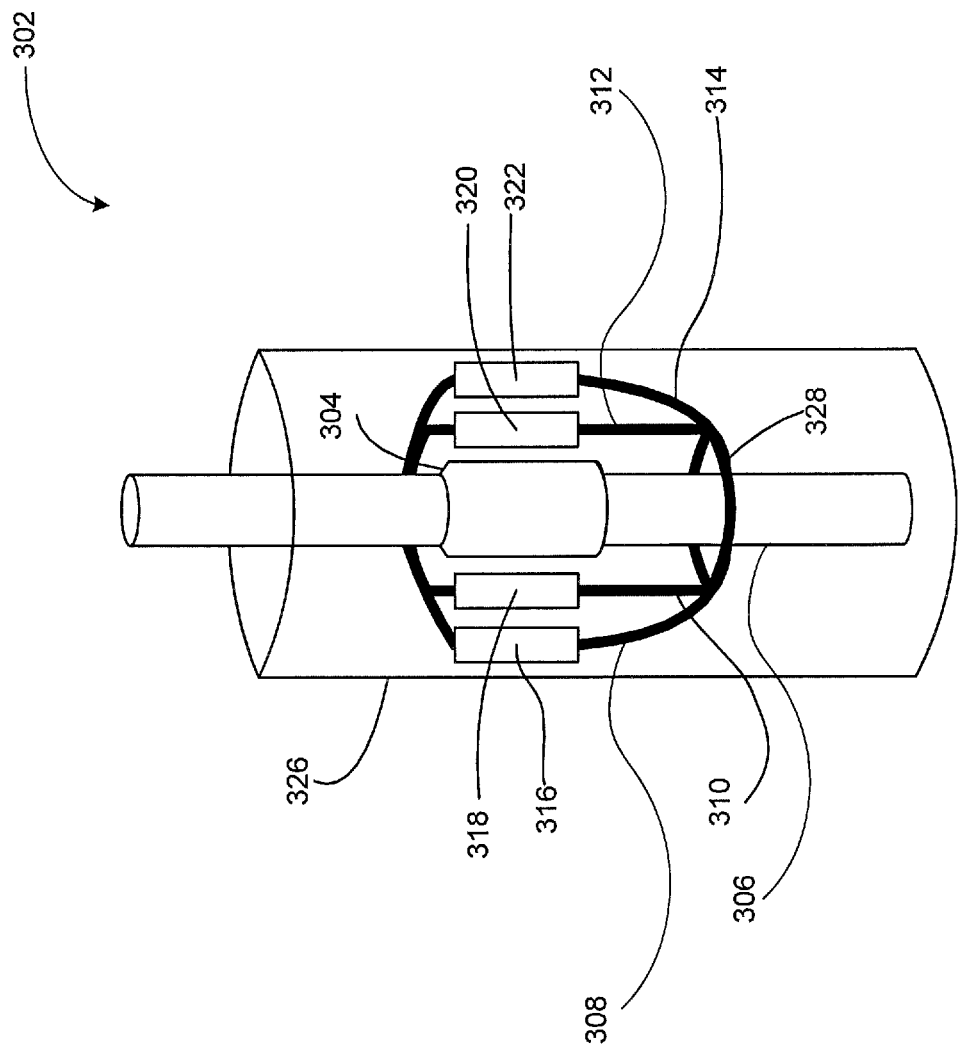

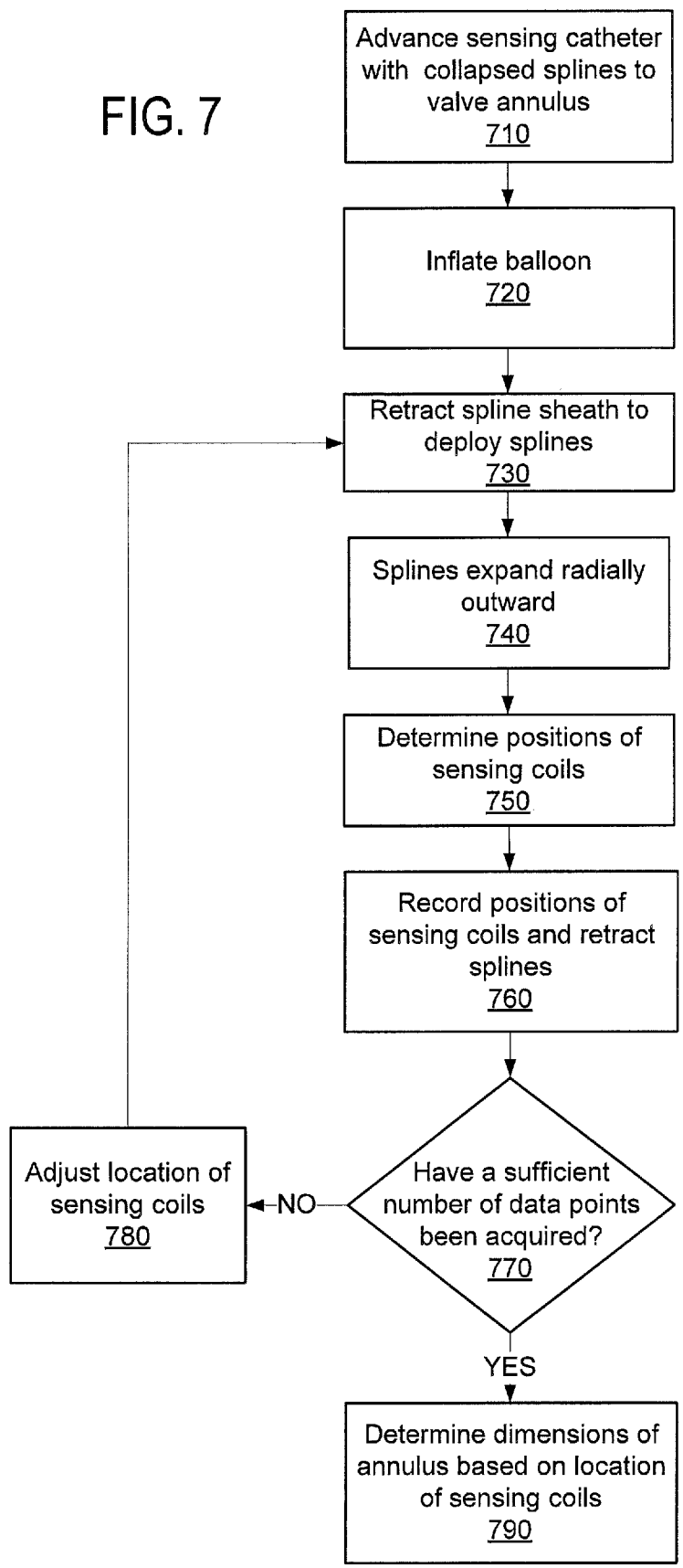

SYSTEM AND METHOD FOR INTRAPROCEDURAL ASSESSMENT OF GEOMETRY AND COMPLIANCE OF VALVE ANNULUS FOR TRANS-CATHETER VALVE IMPLANTATION

CROSS-REFERENCE TO RELATED APPLICATIONS

This application claims the benefit of the filing date of U.S. Provisional Application No. 62/143,968 filed Apr. 7, 2015, the disclosure of which is hereby incorporated by reference herein.

BACKGROUND OF THE INVENTION

Trans-catheter aortic valve replacement ("TAVR") has been shown to improve the survival rate in high risk patients for whom surgical heart valve replacement is not an option. However, the long-term clinical success of a TAVR, or any trans-catheter aortic valve implantation ("TAVI") procedure, is dependent on accurate deployment, anchoring, and acceptable valve performance, both acutely and chronically. This requires maximum reduction, or potential elimination, of the risks associated with paravalvular (PV) aortic regurgitation (AR).

For example, malapposition of the stent frame of a prosthetic valve to the native valve annulus is a major contributing factor for PV AR. In this regard, apposition of the stent may be affected by the degree of calcification of the valve leaflets. Accordingly, highly calcified regions have typically low compliance compared to the non-calcified regions of the native valve annulus. Thus, selecting a proper valve size and assessing the compliance, or lack thereof, of a native valve annulus are important in reducing the risks associated with these procedures. However, determining the proper valve size during a TAVI procedure is difficult due to an inability to easily access the native valve annulus, the presence of calcification and other irregularities, and the eccentricity/elliptical nature of the native valve annulus.

There are a number of ways in which the native valve annulus may be sized in today's clinical practice. They include imaging techniques, such as trans-thoracic echocardiogram (TTE), trans-esophageal echocardiogram (TEE), and angiography. However, these imaging methods are not standardized and may yield different results depending on the view obtained of the native valve annulus with the annulus' elliptical shape contributing to the uncertainty. Although valve sizing using 3D computed tomographic (CT) imaging has been observed to result in less PV AR, this technique is expensive and requires independent patient preparation/assessment prior to the procedure. Additionally, CT imaging exposes the patient to potentially harmful radiation.

Furthermore, alterations to the valve annulus following a balloon valvuloplasty procedure can make it difficult to correctly size the annulus, even with current imaging techniques. Thus, there is a clinical need for an alternative option for accurately sizing a native valve annulus that is cost effective and safe for patients, both before and after a valvuloplasty procedure.

SUMMARY OF THE INVENTION

The disclosed systems and methods enable a physician to assess geometry and compliance of a native valve annulus and thus address the foregoing problems.

In one embodiment, the present disclosure describes a system for determining the dimensions of a native valve annulus is disclosed. The system may include a sensing catheter that has a shaft that extends in a longitudinal direction, a plurality of splines attached to the shaft that have an expanded condition spaced radially outward from the shaft, and a sensing coil located on each of the splines. The system may also include a transmitter to generate a magnetic field to induce a potential in each of the sensing coils and a computing device to provide the positions of the sensing coils based on the induced potentials.

According to another embodiment, the present disclosure describes a method for determining the dimensions of a native valve annulus. The method begins with delivering a sensing catheter to a native valve annulus. The sensing catheter may include a plurality of splines, with each spline having a sensing coil. The plurality of splines may also have a contracted condition and a radially expanded condition. Once the sensing catheter reaches the native valve annulus, the plurality of splines are deployed from the contracted condition to the radially expanded condition. Next, a magnetic field may be generated that induces a potential in each of the sensing coils of the sensing catheter. Accordingly, determining a first position of each of the sensing coils may be determined based on the induced potentials. Based on the locations of each of the sensing coils, a dimension of the native valve annulus may be determined.

Another embodiment of the present disclosure describes an apparatus that includes a shaft extending in a longitudinal direction. A plurality of splines may be attached to the shaft and at least one sensing coil may be located on each of the splines. According to some embodiments, the splines may have an expanded condition spaced radially outward from the shaft. Additionally, the apparatus may have an expandable balloon positioned between the shaft and the plurality of splines.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

FIGS. 3A and 3B are schematic perspective views of a portion of a catheter in which sensing coils are placed on splines extending from the shaft of the catheter according to one aspect of the disclosure.

FIG. 7 is a flow chart depicting a method for determining the locations of sensing coils to determine the geometry of a native valve annulus according to another aspect of the disclosure.

DETAILED DESCRIPTION

As used herein, the words "substantially," "approximately," "generally," and "about" are intended to mean that slight variations from absolute are included within the scope of the structure or process recited. Additionally, the terms "proximal," "distal," "leading," and "trailing" are to be taken as relative to a user using the disclosed catheter. "Proximal" or "trailing end" are to be understood as relatively close to the user and "distal" or "leading end" are to be understood as relatively farther away from the user.

This disclosure provides for a system and method for assessing geometry and compliance of a native valve annulus. In particular, the native valve annulus may be a valve annulus in which a trans-catheter aortic valve is to be implanted. The native valve annulus may also be that in which another type of trans-catheter cardiac valve is to be implanted, such as a mitral valve, a tricuspid valve, or a pulmonary valve. Alternatively, the native valve annulus may refer to a prosthetic valve previously implanted in a patient which has subsequently become diseased, requiring further intervention using a new trans-catheter valve implantation procedure ("valve-in-valve" implantation). The disclosed system and method use sensing coils to detect generated magnetic fields to determine the dimensions and compliance of the native valve annulus. The systems and methods described herein can be used to determine dimensions and compliance of the valve annulus post valvuloplasty and prior to prosthetic valve implantation.

During balloon valvuloplasty, a balloon catheter positioned in the native valve annulus is inflated with saline, flattening the native valve leaflets, which are typically diseased and/or calcified. A non-compliant balloon is typically used for this purpose.

Figure 1:
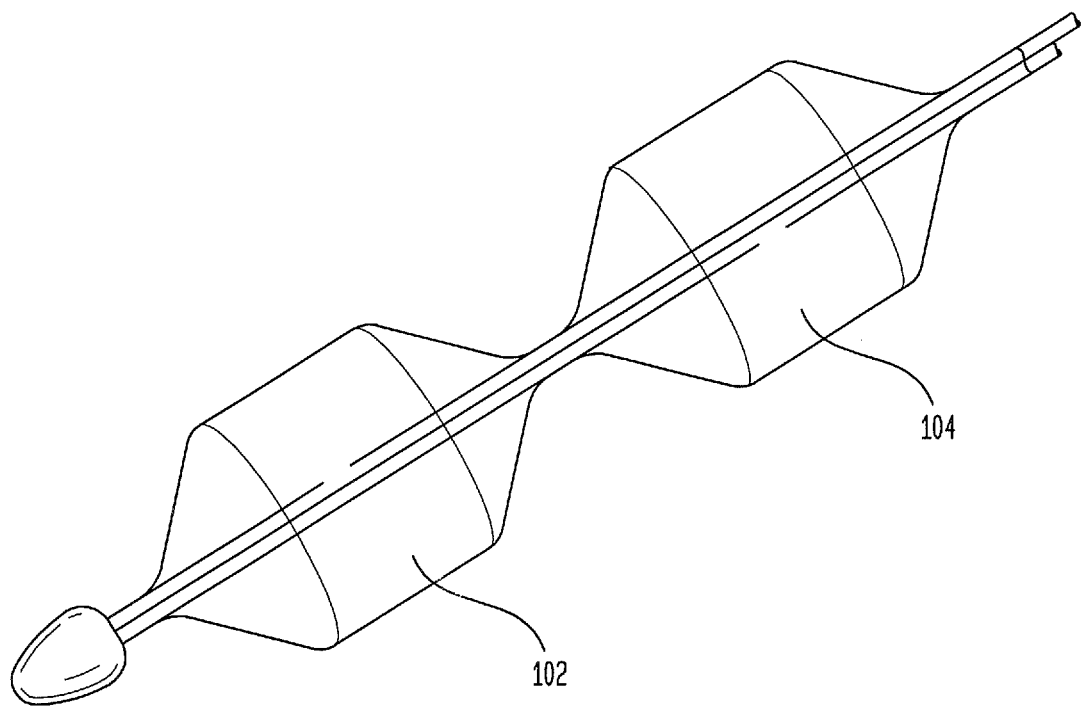
FIG. 1 is a perspective view of an exemplary balloon catheter according to aspects of the disclosure.

In one embodiment, the disclosed system and method may add another balloon, typically a compliant balloon, either proximal or distal to the valvuloplasty balloon. FIG. 1 illustrates one example of a non-compliant balloon 102 having a compliant balloon 104 placed adjacent to it. According to one embodiment, the operator may inflate and deflate the non-compliant balloon 102 to perform a balloon valvuloplasty procedure, then either advance or retract the catheter and inflate the compliant (i.e., sizing) balloon 104 to measure the dimensions of the native valve annulus. By locating the compliant balloon proximally or distally to the valvuloplasty balloon, quicker exchange and reduced procedure times may be achieved.

The compliant balloon 104 may share a fluid lumen with the non-compliant balloon 102. Alternatively, the fluid lumens may be separate. When inflated, the compliant balloon 104 may conform to the native valve annulus such that the walls of the balloon 104 contact substantially the entire circumference of the native valve annulus or as much of the circumference of the native valve annulus as is physically possible (e.g., there may be slight gaps between the balloon wall and the circumference of the native valve annulus). In cases in which valvuloplasty is not performed prior to valve implantation, a device incorporating only a compliant balloon may be used for sizing the native valve annulus.

Figure 2:
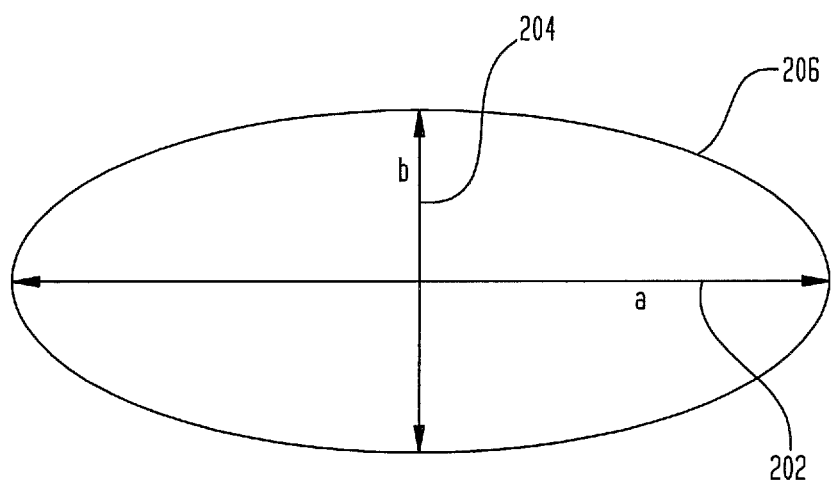
FIG. 2 is a diagrammatic view illustrating the elliptical dimensions of a native valve annulus that may be determined according to aspects of the disclosure.

FIG. 2 illustrates an example of the dimensions of the native valve annulus that may be measured by the systems and methods described herein. In one embodiment, sizing of the native valve annulus with a sizing balloon may be performed by determining the positions, such as location and orientation, of sensing coils positioned within the native valve annulus. The positions of the sensing coils may be stored in a memory or displayed (or both). The sensing coils may then be repositioned and redeployed in the native valve annulus. Again, the positions of the sensing coils may be determined and stored. The system may connect the various data points via line segments or smooth curves to form an ellipse around the data points. With this procedure, the dimensions of the native valve annulus may be determined. The dimensions may include the major axis length 202, a minor axis length 204, perimeter 206, area, area and perimeter averaged length of the annulus. According to some embodiments, the major axis length 202 and the minor axis length 204 may be approximated or estimated and within a degree of confidence. From these dimensions, other aspects of the native valve annulus may also be determined, such as its eccentricity.

Figure 3B:
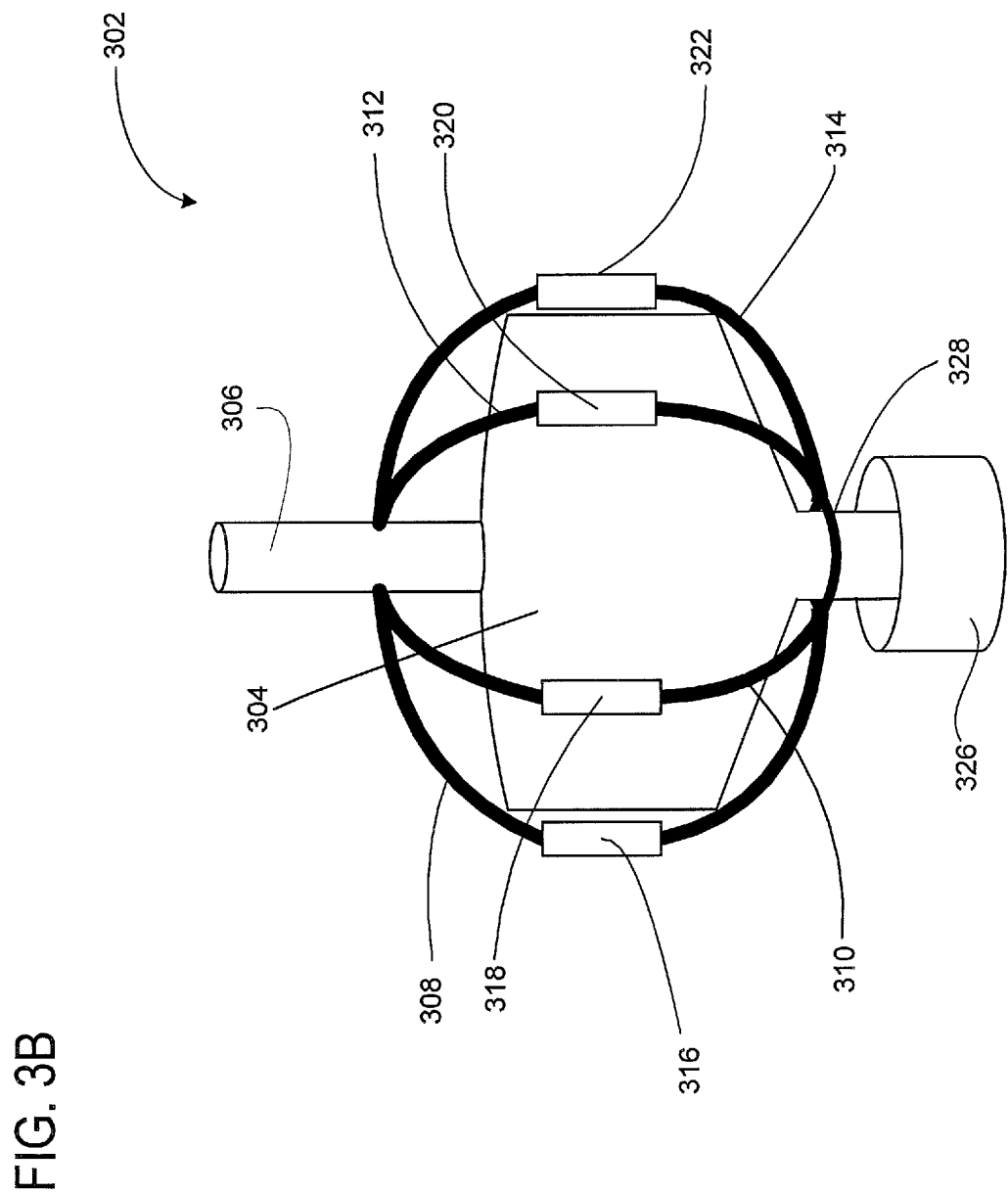

FIGS. 3A and 3B are schematic perspective views of a sensing catheter 302 according to one aspect of the disclosure. The sensing catheter may include a shaft 306 having a leading end and a trailing end. In some embodiments, shaft 306 may have a lumen for a guide wire. A plurality of splines 308, 310, 312, and 314 may be attached in an array near the leading end of shaft 306. More particularly, the end of each spline closest to the leading end of shaft 306 may be fixedly attached to the shaft. The other end of each spline may be attached to a ring 328 that is free to slide on shaft 306. While splines 308, 310, 312, and 314 are shown as fixedly attached to the leading end of shaft 306 and the ring 328, one of ordinary skill in the art would recognize that other orientations may be employed. For example, splines 308, 310, 312, and 314 may be fixedly attached to a trailing portion of shaft 306 and to ring 328, which may be slidably mounted toward the leading end of shaft 306.

As splines 308, 310, 312 and 314 are deployed by retracting a spline sheath 326 (as described in greater detail below), they will bow radially outwardly from shaft 306 to an expanded condition. This outward bowing will cause ring 328 to slide in a distal direction toward the leading end of shaft 306. Conversely, during re-sheathing the sliding ring 328 will move proximally and the splines 308, 310, 312, and 314 will move from the expanded condition radially inward to a contracted condition closer to shaft 306. The ease with which splines 308, 310, 312 and 314 may be moved between the contracted and expanded conditions enables their easy deployment and re-sheathing without causing significantly large residual stresses.

In some embodiments, splines 308, 310, 312, and 314 may be struts formed from a shape-memory material, such as Nitinol, and heat set in an expanded condition so that the spline array self-expands to the expanded condition upon deployment. When unconstrained, the spline array may expand radially outward to a diameter that is larger than the largest cardiac valve annulus diameter (typically around 30 mm for the aortic valve in humans). The diameter of the expanded spline array may be between about 1 FR and about 3 FR. Preferably, the diameter of the expanded spline array may be about 2 FR. While four splines are shown in FIGS. 3A and 3B, sensing catheter 302 may have any number of splines spaced around shaft 306. According to preferred embodiments, the splines may be equally-spaced around shaft 306.

Each spline may have at least one sensing coil mounted thereon. As shown in FIGS. 3A and 3B, a first sensing coil 316 may be mounted on spline 308, a second sensing coil 318 may be mounted on spline 310, a third sensing coil 320 may be mounted on spline 312, and a fourth sensing coil 322 may be mounted on spline 314. The sensing coils may be any sensing coils suitable for medical purposes and capable of measuring induced voltage due to variations in magnetic flux. In some embodiments, sensing coils 316, 318, 320, and 322 may be mounted along the waist or expansion center (i.e., equator) of each spline. In another embodiment, the sensing coils may be located in different planes perpendicular to the shaft 306 to provide three-dimensional information of the native valve annulus. In a further embodiment, multiple sensing coils may be positioned on each spline to obtain three-dimensional information relevant to the valve annulus. The sensing coils may be between about 0.5 mm and about 4.5 mm long. In preferred embodiments, the sensing coils may be about 1 mm long.

As noted above, sensing catheter 302 may include a spline sheath 326 that is allowed to slide relative to shaft 306 and to splines 308, 310, 312 and 314. The spline sheath may keep the splines in the contracted condition, shown in FIG. 3A, as the sensing catheter is delivered to a native valve annulus. After the sensing catheter is advanced to the native valve annulus, spline sheath 326 may be retracted using any known technique to deploy the splines to the expanded condition shown in FIG. 3B.

According to the embodiment shown in FIGS. 3A and 3B, the sensing catheter may include a non-compliant or semi-compliant balloon 304 formed of a suitable material positioned inside of splines 308, 310, 312 and 314. The ends of balloon 304 may be bonded to shaft 306. A fluid lumen and aperture (not shown) in shaft 306 may supply a pressurized homogeneous medium (e.g., saline) for inflating balloon 304. Upon full inflation of balloon 304, a small incremental additional pressure may be applied to the balloon 304, resulting in a small and measureable displacement of the sensing coils on the splines. The relative displacement of the sensing coils in response to the additional pressure can be used to assess the compliance of the annulus. Thus, by using either a compliant, non-compliant, or semi-compliant balloon, sensing catheter 302 may determine the dimensions of the native valve annulus, whereas using a non-compliant or semi-compliant balloon allows the sensing catheter 302 to determine both the dimensions and the compliance of the native valve annulus.

Figure 4:
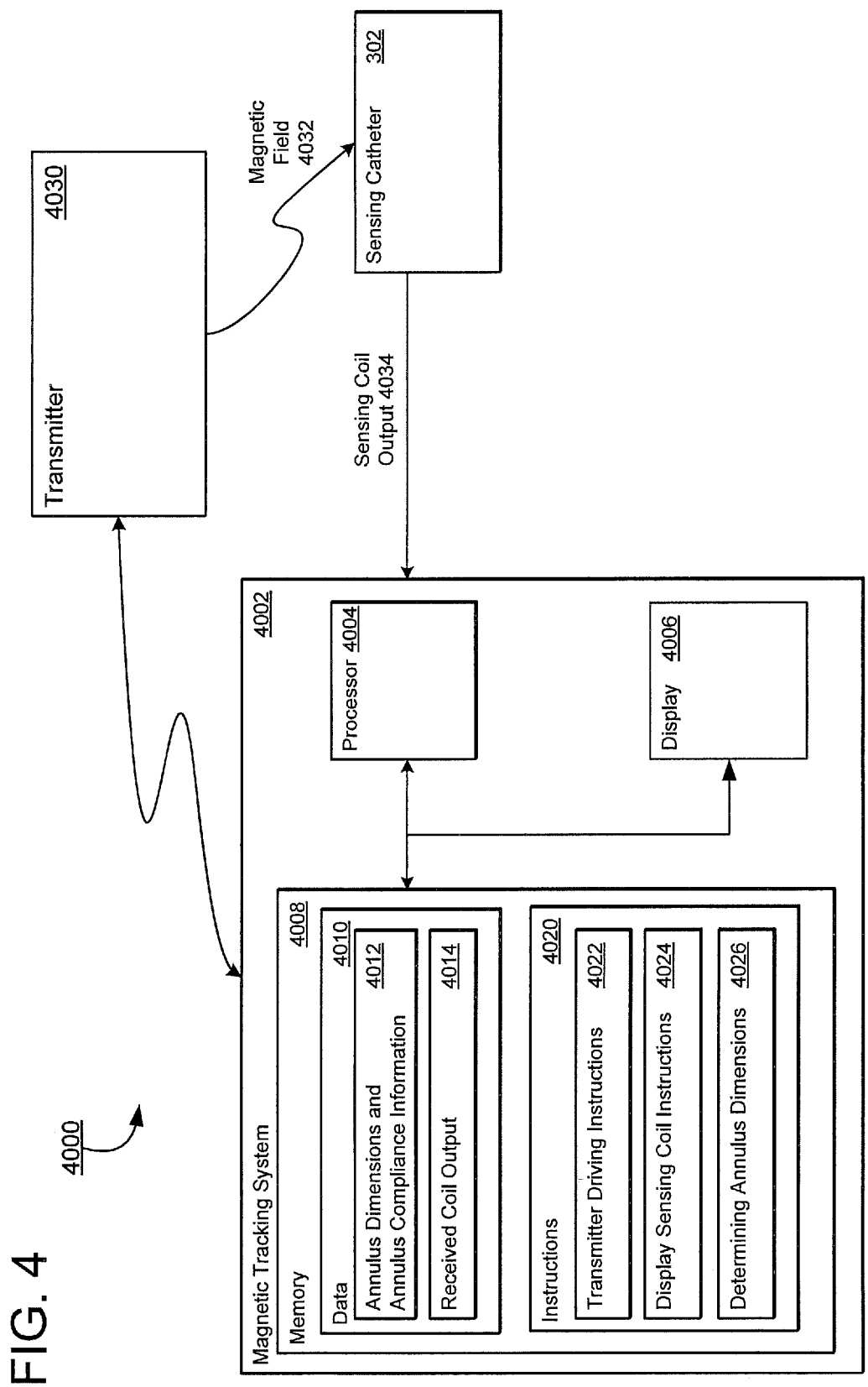
FIG. 4 is a block diagram illustrating an exemplary system for determining the dimensions of a native valve annulus according to aspects of the disclosure.

FIG. 4 illustrates an exemplary system 4000 for detecting the positions of the sensing coils deployed via the sensing catheter and for determining from those positions the dimensions, eccentricity, and compliance of a native valve annulus. The system 4000 may include a magnetic tracking system 4002, a transmitter 4030, and the sensing catheter 302.

The magnetic tracking system 4002 may include a processor 4004, a display 4006, and a non-transitory, computer-readable memory 4008. The magnetic tracking system 4002 may be a personal computer, intended for use by a user, having all the components normally found in a personal computer, such as a central processing unit (CPU), display device, CD-ROM, hard drive, user inputs, speakers, modem and/or network interface device, and all of the components used for connecting these elements to one another. Alternatively, the magnetic tracking system 4002 may be any computing device, such as a server, tablet, mobile device, smart phone, phablet, etc. In other examples, the magnetic tracking system 4002 may be specialized computing equipment, such as a Mediguide® system (available from Mediguide Ltd. of Haifa, Israel). The magnetic tracking system 4002 may be in communication with transmitter 4030 and sensing catheter 302.

The processor 4004 may be any conventional processor, such as a commercially available CPU. Alternatively, the processor 4004 may be a dedicated device, such as an Application Specific Integrated Circuit (ASIC), a Field Programmable Gate Array (FPGA), or other programmable, hardware-based processor. Additionally, the processor 4004 may include multiple processors, multi-core processors, or a combination thereof. Accordingly, references to a processor will be understood to include references to a collection of processors or dedicated logic that may or may not operate in parallel.

The display 4006 may include any display capable of rendering data visually. For example, the display 4006 may include a monitor, such as an LED or plasma display. In some embodiments, display 4006 may represent the positions of the sensing coils dynamically in real time at 10-30 frames per second. While display 4006 is shown as a component integrated into magnetic tracking system 4002, one of ordinary skill in the art would recognize that display 4006 may be a stand-alone device. Further, display 4006 may be located remotely from the magnetic tracking system 4002. For example, the data gathered by magnetic tracking system 4002 may be transmitted over a network to display 4006 to be viewed remotely.

The memory 4008 may be any memory capable of storing information accessible by the processor 4004, including data 4010 and instructions 4020 that may be executed or otherwise used by the processor. In this regard, the memory 4008 may be of any type capable of storing information accessible by the processor, including a non-transitory, computer-readable medium, or other medium that stores data that may be read with the aid of an electronic device, such as a hard-drive, memory card, flash drive, ROM, RAM, DRAM, DVD or other optical disks, as well as other write-capable and read-only memories. The memory may include short term or temporary storage as well as long term or persistent storage. Alternatively, the memory 4008 may include a storage area network (SAN) capable of being accessed by magnetic tracking system 4002. Storage systems and methods may include different combinations of the foregoing, whereby different portions of the instructions and data may be stored on different types of media.

The data 4010 may include annulus dimensions and compliance information 4012 and received coil output 4014 from the sensing catheter 302. The data 4010 may be retrieved, stored, or modified by processor 4004 in accordance with instructions 4020. Additionally, the data 4010 may be outputted to display 4006 in accordance with instructions 4020. The data may be formatted in any computer-readable format, and may comprise any information sufficient to identify the relevant information, such as numbers, descriptive text, proprietary codes, references to data stored in other areas of the same memory or different memories (including other network locations) or information that is used to calculate the relevant data.

The instructions 4020 may be any set of instructions to be executed by the processor 4004. For example, the instructions may be stored as computer code on the non-transitory, computer-readable medium. The terms "instructions," "modules," and "programs" may be used interchangeably herein. The instructions may include instructions 4022 for driving the transmitter, instructions 4024 for determining and displaying the positions of the sensing coils and instructions 4026 for determining the dimensions, eccentricity and compliance of an annulus from the measured potentials. Functions, methods and routines of the instructions are explained in more detail below.

The transmitter 4030 may be any transmitting device capable of generating a number of distinct magnetic fields 4032. For example, the transmitter 4030 may include an array of drive coils at fixed and previously established locations proximate to the navigation region of interest. In some embodiments, the transmitter 4030 may be located beneath a patient's bed, mounted to the side of a patient's bed, or located on another instrument, such as a fluoroscopy head. The transmitter may generate magnetic fields, typically in a range of 1 to 20 kilohertz. Accordingly, each drive coil may induce potentials in the sensing coils of the sensing catheter 302 by virtue of slightly different drive frequencies for each drive coil. If enough degrees-of-freedom are provided by using a sufficient number of drive coils (i.e., at least 6, but commonly 9 or more), the location and orientation of any sensing coil in a catheter or other instrument may be determined in real time. Thus, the magnetic tracking system may determine the location and/or orientation of each of the sensing coils in catheter 302 described above. Sub-millimeter accuracy of the location and orientation of the coils has been established using the Mediguide® system. While the transmitter 4030 is illustrated as a separate component from the magnetic tracking system 4002, one of ordinary skill in the art would recognize that the magnetic tracking system 4002 and the transmitter 4030 may be located in the same housing.

Figure 5:
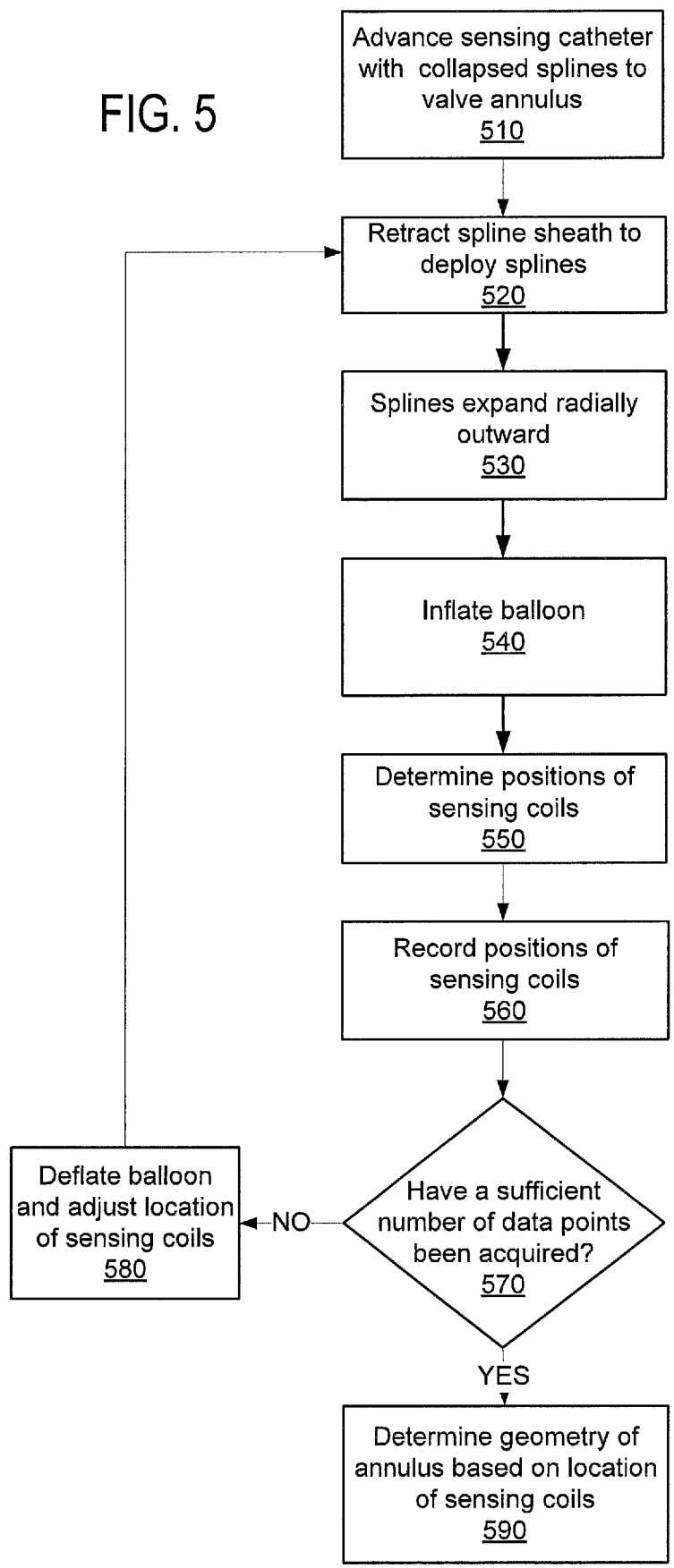
FIG. 5 is a flow chart depicting a method for determining the locations of sensing coils to determine the geometry of a native valve annulus according to one aspect of the disclosure.

FIG. 5 illustrates a method for assessing the cross-sectional dimensions and compliance of a native valve annulus which may be performed using system 4000 or any other capable system. In block 510, sensing catheter 302, with balloon 304 deflated and splines 308, 310, 312 and 314 in a collapsed state, may be advanced to the native valve annulus over a guide wire. Once the sensing catheter is in the appropriate location, spline sheath 326 may be retracted in block 520 to deploy the splines. In block 530, the splines expand radially outward as they are deployed until sensing coils 316, 318, 320 and 322 contact the periphery of the native valve annulus.

Once deployment of the splines has been achieved, balloon 304 may be inflated in block 540 using saline or other fluid. As balloon 304 inflates, it may conform to the shape of the native valve annulus. In doing so, balloon 304 may push one or more of splines 308, 310, 312 and 314 outwardly to ensure that each of sensing coils 316, 318, 320 and 322 is in contact with the native valve annulus.

With the splines deployed and the balloon inflated, system 4000 may be employed to determine the positions of the sensing coils and, from that information, the size and shape of the native valve annulus. More particularly, in block 550, magnetic tracking system 4002 may be used to determine the three-dimensional positions of sensing coils 316, 318, 320 and 322. Magnetic tracking system 4002 may send instructions to transmitter 4030 to begin generating magnetic fields 4032. Each drive coil in transmitter 4030 may use a slightly different drive frequency to generate a number of distinct magnetic fields at fixed and previously established locations proximate to the navigation region of interest. Each distinct magnetic field may generate a potential at each of the sensing coils. The potentials induced in the sensing coils may be transmitted to the magnetic tracking system 4002 as sensing coil output 4034. The magnetic tracking system 4002 may amplify the sensing coil output 4034 and convert it to a real time digital amplitude representation. According to some embodiments, the position (e.g., location, orientation, etc.) of any sensing coil in a catheter or other instrument may be determined in real time. In this regard, the magnetic tracking system 4002 may determine the location and/or orientation of each of the sensing coils and output the location and/or orientation of each of the sensing coils via display 4006.

In some embodiments, determining the position of each sensing coil may include representing the position of each sensing coil graphically on a display or another computing device, such as a computer, tablet, etc. As noted above, the positions of the sensing coils may be represented dynamically in real time at 10-30 frames per second. Displaying the sensing coils in real time may provide an indication of the degree of calcification of the native valve annulus. For example, the sensing coils that are less dynamic or that traverse a shorter distance during a cardiac cycle may indicate a greater degree of calcification in that region of the valve annulus.

In block 560, the positions of the sensing coils may be recorded either by storing them in memory or plotting them graphically, for example, on a Cartesian plane. In block 570, a determination is made with respect to whether enough data points have been collected. For example, the system may need a predetermined number of sensing coil locations to provide an accurate measurement of the native valve annulus. If an insufficient number of data points have been collected, in block 580, balloon 304 may be deflated and sheath 326 advanced to move the splines 308, 310, 312 and 314 to the collapsed condition. The catheter may then be rotated and the process of deploying the splines and acquiring the positions of the sensing coils in the same plane of the native valve annulus as the first data set is repeated. If the system determines in block 570 that the predetermined number of data points have been collected, in block 590 the system determines the geometry of the annulus based on the determined locations of the sensing coils.

Figure 6A:
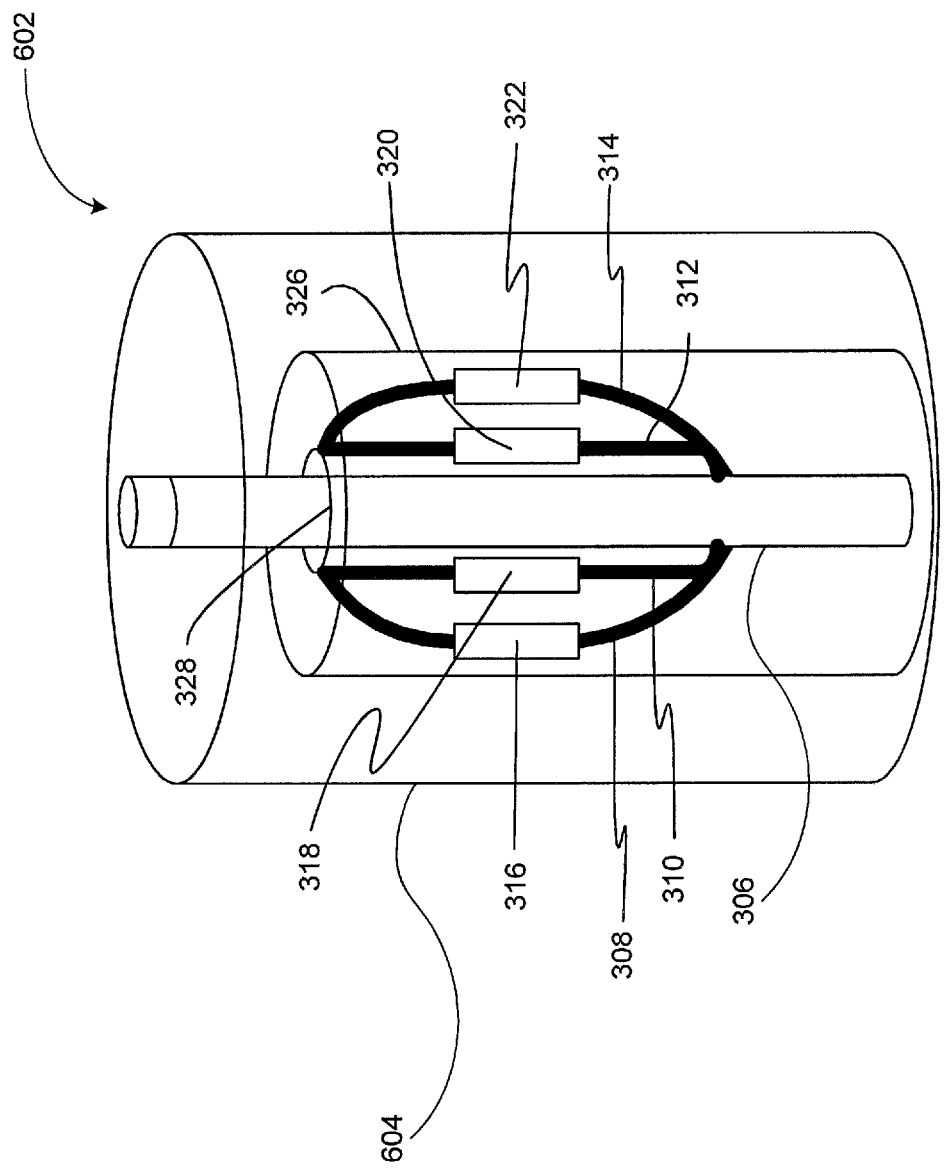
FIGS. 6A and 6B are schematic perspective views of a portion of a catheter in which sensing coils are placed on splines extending from the shaft of the catheter according to another aspect of the disclosure.
Figure 6B:
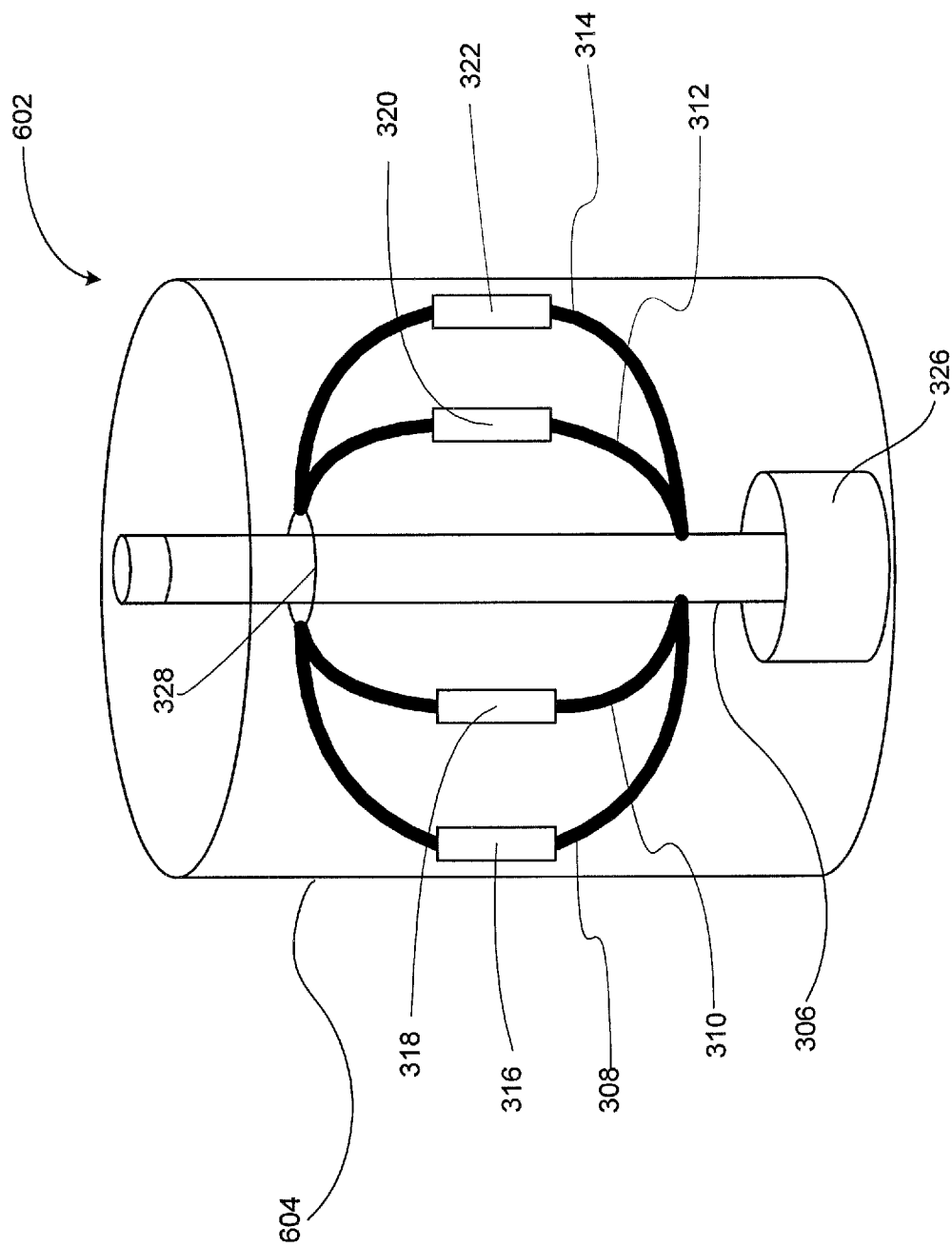

FIGS. 6A and 6B are schematic perspective views of a sensing catheter 602 according to another aspect of the disclosure. Sensing catheter 602 is similar to sensing catheter 302 described above with respect to FIGS. 3A and 3B.

However, sensing catheter 602 differs from sensing catheter 302 in that the sensing coils are located within balloon 604.

According to the embodiment shown in FIGS. 6A and 6B, balloon 604 may be a compliant balloon. By using a compliant balloon, sensing catheter 602 may hold the leaflets of the native valve annulus back and prevent the leaflets from prolapsing. Moreover, the compliant balloon will conform to the shape of the native valve annulus.

Turning to FIG. 6A, sensing catheter 602 is shown with balloon 604 in a deflated state and the splines maintained in a contracted condition by spline sheath 326. A fluid lumen and aperture in shaft 306 (not shown) may supply a pressurized homogeneous medium (e.g., saline) for inflating balloon 604. Upon full inflation of balloon 604, spline sheath 326 may be retracted using any known technique, thereby allowing splines 308, 310, 312, and 314 to expand radially outward as shown in FIG. 6B. Splines 308, 310, 312, and 314 may expand outwardly such that sensing coils 316, 318, 320, and 322 contact the inner wall of balloon 604. Accordingly, sensing coils 316, 318, 320, and 322 may be used to determine the dimensions of the native valve annulus.

FIG. 7 illustrates a method for assessing the cross-sectional dimensions of a native valve annulus using the sensing catheter depicted in FIGS. 6A and 6B, which may be performed using system 4000 or any other capable system. In block 710, the sensing catheter, with the balloon deflated and the splines in a collapsed state, may be advanced to the native valve annulus over a guide wire.

In block 720, balloon 604 may be inflated such that it conforms to the shape of the native valve annulus. After balloon 604 has been fully inflated, spline sheath 326 may be retracted in block 730 to deploy the splines. In block 740, the splines expand radially outward as they are deployed until the sensing coils contact the inner wall of balloon 604.

As described above, system 4000 may be employed to determine the positions of the sensing coils and, from that information, the size and shape of the native valve annulus. For example, in block 750, magnetic tracking system 4002 may be used to determine the three-dimensional positions of sensing coils 316, 318, 320, and 322 by representing the position of each sensing coil graphically on a display.

The positions of the sensing coils may be recorded in memory or plotted graphically in block 760, and sheath 326 may be advanced to move splines 308, 310, 312, and 314 to the collapsed state. In block 770, a determination is made whether enough data points have been collected regarding the native valve annulus. If an insufficient number of data points have been collected, the location of the sensing coils may be adjusted in block 780. For example, the location of the sensing coils may be adjusted by rotating the sensing coils in balloon 604. Accordingly, the process of deploying the splines and acquiring the positions of the sensing coils in the same plane of the native valve annulus as the first data set is repeated. However, if the system determines in block 770 that a sufficient number of data points have been collected, the system determines the dimensions of the annulus based on the determined locations of the sensing coils in block 790.

Figure 8A:
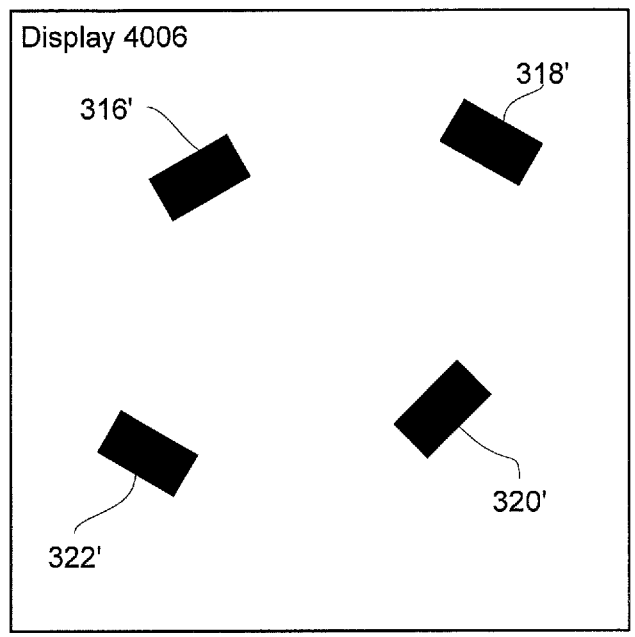
FIGS. 8A-8C are diagrammatic views illustrating a display of the sensing coils according to one aspect of the disclosure.
Figure 8B:
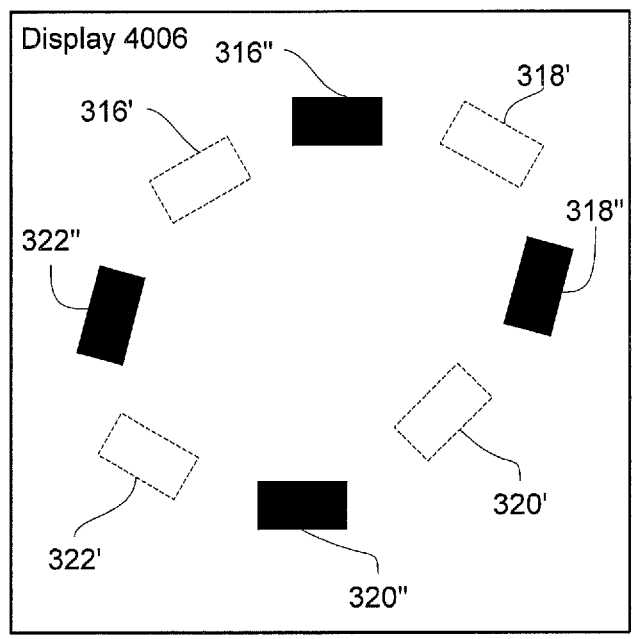
Figure 8C:
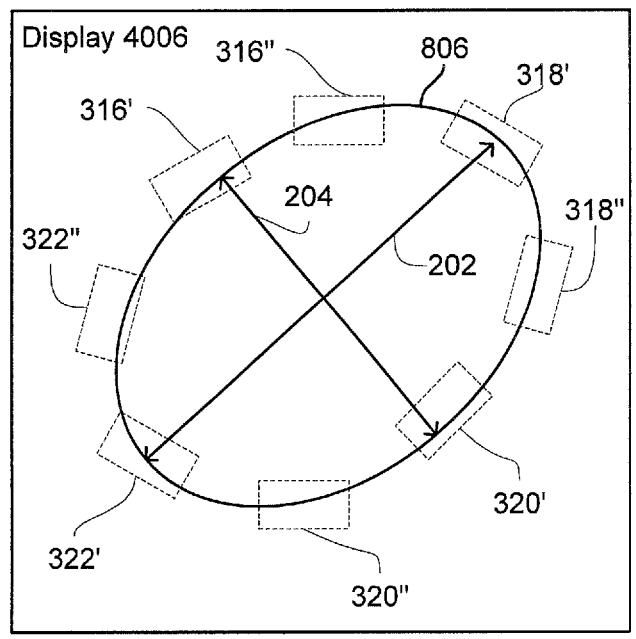

FIGS. 8A-8C illustrate an example of determining the geometry of the native valve annulus in accordance with the methods described above. FIG. 8A shows the positions of the sensing coils on the display 4006. The first location of the first sensing coil 316 may be indicated by the data point 316', the first location of the second sensing coil 318 may be indicated by the data point 318', the first location of the third sensing coil 320 may be indicated by the data point 320', and the first location of the fourth sensing coil 322 may be indicated by the data point 322'. As noted above, the position of the sensing catheter may be adjusted to acquire another set of data points in the same plane. FIG. 8B shows the second location of the first sensing coil 316 as indicated by the data point 316", the second location of the second sensing coil 318 as indicated by the data point 318", the second location of the third sensing coil 320 as indicated by the data point 320", and the second location of the fourth sensing coil 322 as indicated by the data point 322".

In one embodiment, after a predetermined number of data points have been collected, the system may connect adjacent data points with line segments or a smooth curve to create a visual image of the valve annulus cross-section. In another embodiment, a smooth curve is fitted to the set of points collected. In yet another embodiment, an ellipse can be fitted to the set of data points. FIG. 8C shows an example of the geometry of a native valve annulus as determined by the foregoing procedure. In particular, FIG. 8C illustrates a smooth curve 806 fitted to the set of data points.

Smooth curve 806 may represent the perimeter of the native valve annulus. Further, the major axis length 202 and the minor axis length 204 may be determined from the set of data points collected. Accordingly, the information displayed in FIG. 8C may be used to determine additional information for the native valve annulus, such as the area and area and perimeter averaged length of the annulus.

Figure 9:
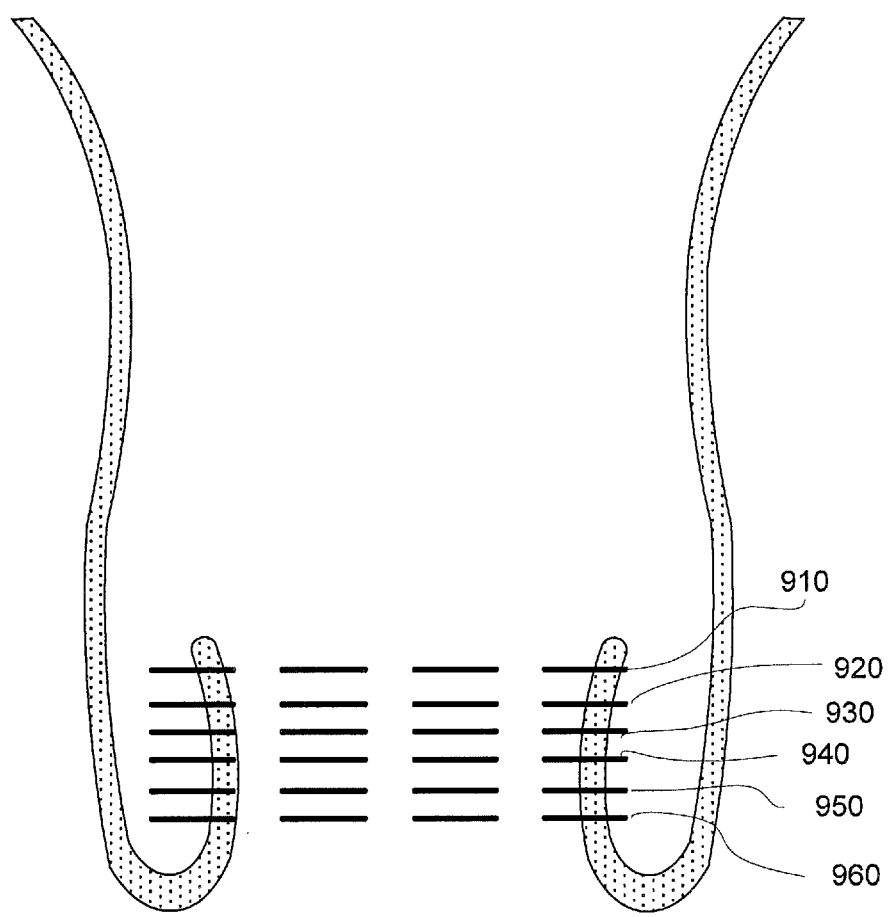
FIG. 9 is a diagrammatic view illustrating an example of determining the three-dimensional geometry of a native valve annulus according to aspects of the disclosure.

Additionally, the sensing catheters described herein may be used to obtain three-dimensional information about the native valve annulus. Referring to FIG. 9, a cross-section of a native aortic valve is shown. Three-dimensional information for the valve may be constructed by determining the valve geometry, as described above, at different planes of the native valve annulus (e.g., at planes 910, 920, 930, 940, 950, and 960). For example, the method depicted in either FIG. 5 or 7 may be performed at a first plane 910. The catheter may then be translated so that the sensing coils are at about plane 920, and the method may be repeated. The catheter may again be translated and the method repeated at each of the remaining planes (e.g., 930, 940, 950, and 960). The information gathered at each plane may be collated to develop three-dimensional information for the native valve annulus. The three-dimensional information may be used to decide the best landing spot for the deployment of a prosthetic valve, thereby minimizing paravalvular leakage when an appropriately-sized transcatheter valve is used. The three-dimensional information may be depicted graphically or numerically, depending on the needs of the user.

Figure 10:
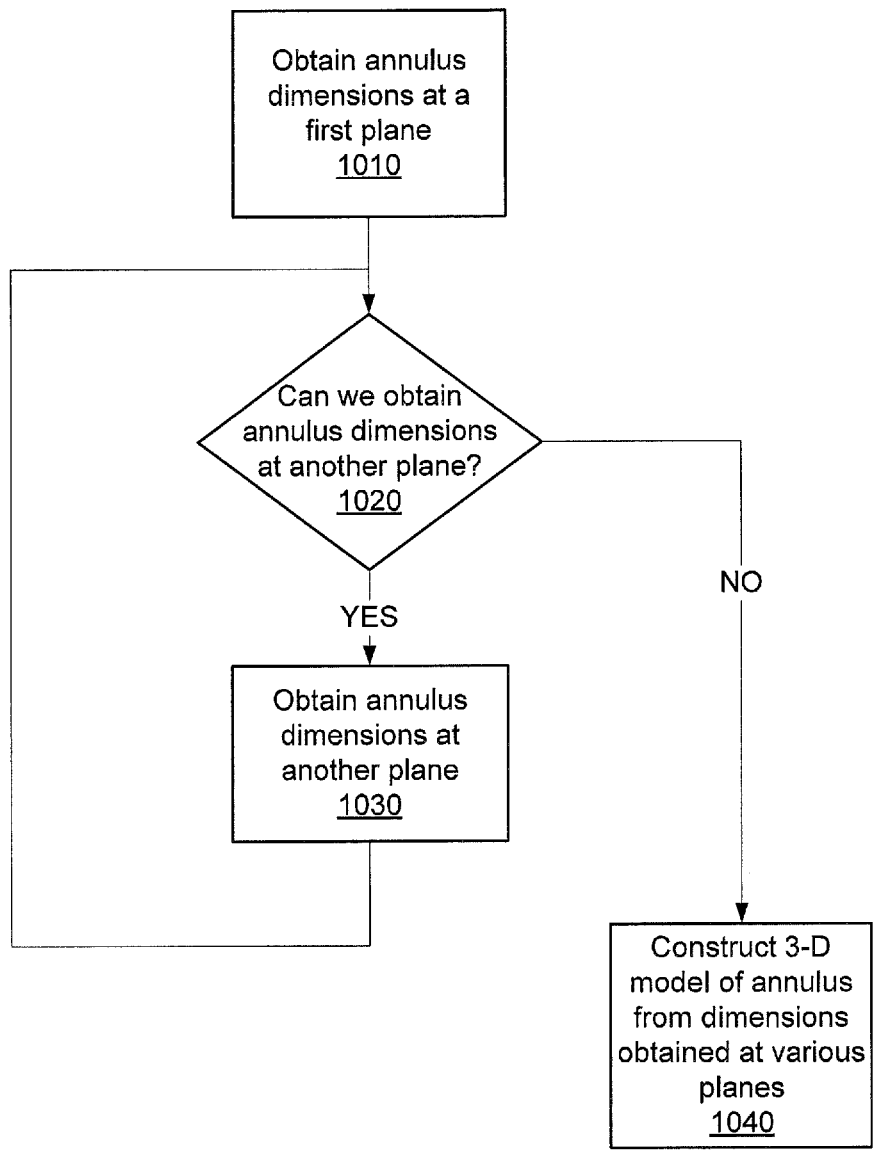
FIG. 10 is a flow chart depicting a method for determining the three-dimensional geometry of a native valve annulus according to aspects of the disclosure.

Turning to FIG. 10, an exemplary flow chart of a method for obtaining three-dimensional information about the native valve annulus is shown. In block 1010, the sensing catheter may obtain the dimensions of the native valve annulus at a first plane. The steps to obtain those dimensions may be those depicted in the flow chart of either FIG. 5 or 7. In block 1020, a determination is made as to whether the dimensions of the native valve annulus may be obtained at a different plane. If it is determined that the dimensions at an additional plane may be obtained, the method proceeds to block 1030 at which the dimensions at another plane are obtained. The inquiry performed in block 1020 may be performed repeatedly until there are no additional planes at which to obtain dimensions of the native valve annulus. If it is determined that there are no other planes at which the dimensions of the native valve annulus can be obtained, then the method proceeds to block 1040 at which a 3-D model of the native valve annulus is constructed from the dimensions obtained at the various planes. Alternatively, the 3-D model of the native valve annulus may be constructed after the geometry at a predetermined number of planes has been obtained.

Figure 11A:
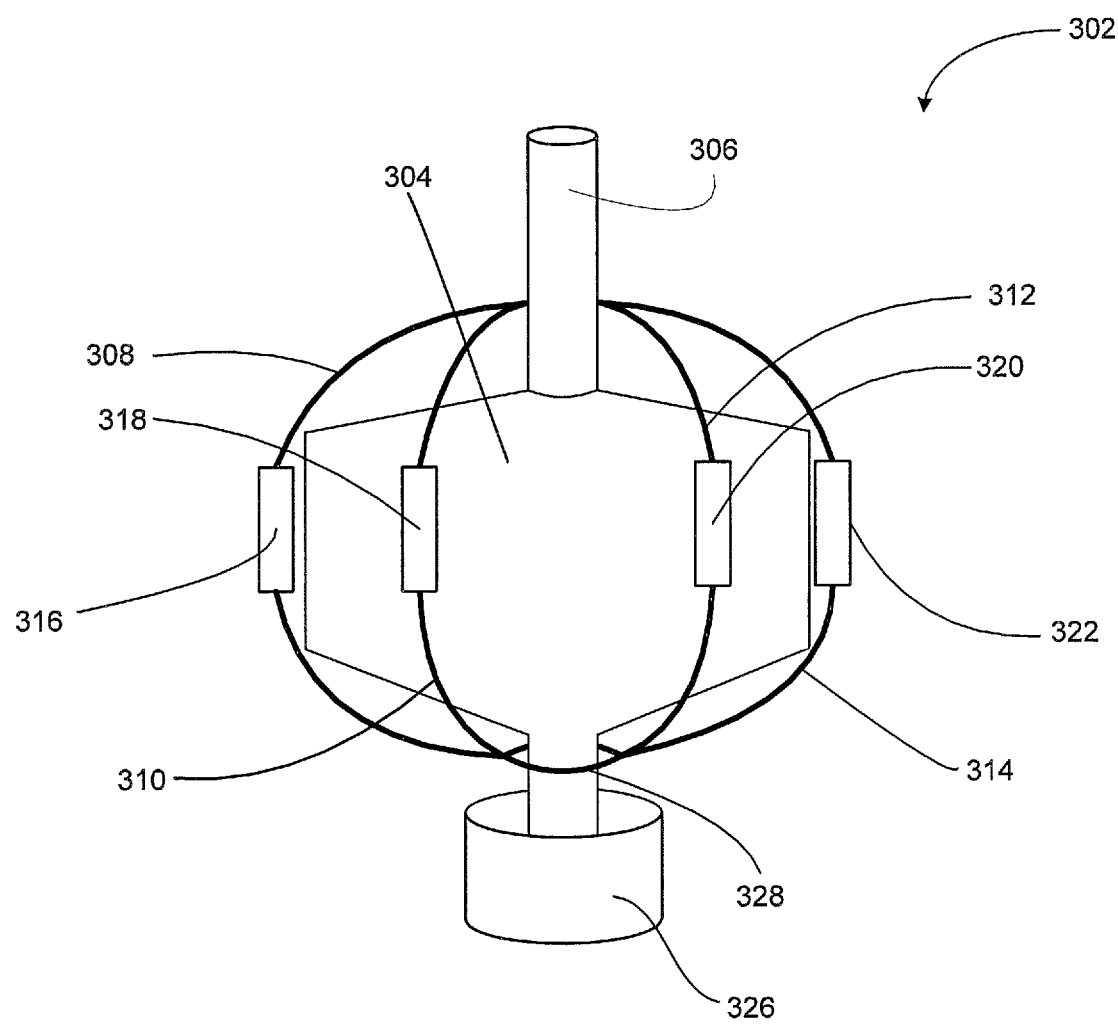
FIGS. 11A and 11B are schematic perspective views of a portion of a balloon catheter in which sensing coils are placed on splines extending from the shaft of the catheter according to one aspect of the disclosure.
Figure 11B:
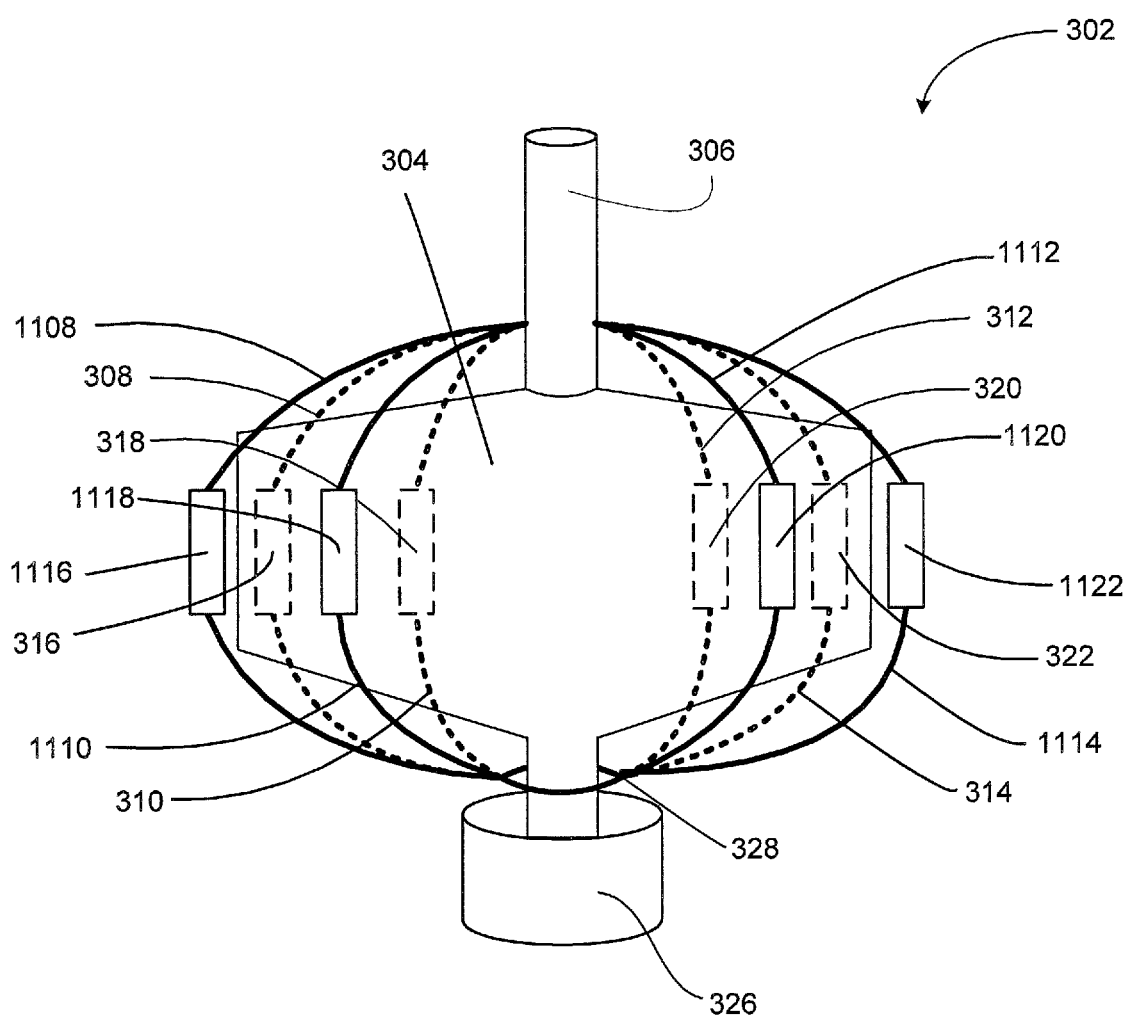

According to another embodiment, a sensing balloon catheter may be used to determine the relative compliance of the native valve annulus. FIGS. 11A and 11B are schematic perspective views showing the use of sensing balloon catheter 302 described above (i.e., with balloon 304 positioned inside of splines 308, 310, 312 and 314) to determine the compliance of the native valve annulus. FIG. 11A shows the sensing balloon catheter 302 after spline sheath 326 has been retracted and non- or semi-compliant balloon 304 has been inflated to a first inflated condition. In this first deployment, baseline locations of sensing coils 316, 318, 320, and 322 may be determined using the methods described above.

FIG. 11B illustrates the sensing balloon catheter 302 in a second inflated condition in which balloon 304 is at a greater pressure. As a result of this greater pressure, balloon 304 may exert a uniform pressure on the native valve annulus similar to the radial force that a stent frame would exert on the native valve annulus. Where the native valve annulus is compliant, the pressure exerted by the balloon may force the annulus radially outward, whereas noncompliant calcified portions of the annulus will not deform or will deform to a much lesser extent. In those areas in which the annulus moves outward, the balloon will also expand radially, enabling selected ones of the splines to further expand outwardly. Depending on which of the splines expand outwardly, one or more (or none) of sensing coils 316, 318, 320, and 322 may be displaced. For example, sensing coil 1116 shows the displacement of sensing coil 316 after balloon 304 has been further inflated. Similarly, sensing coil 1118 shows the displacement of sensing coil 318; sensing coil 1120 shows the displacement of sensing coil 320; and sensing coil 1122 shows the displacement of sensing coil 322.

Figure 12:
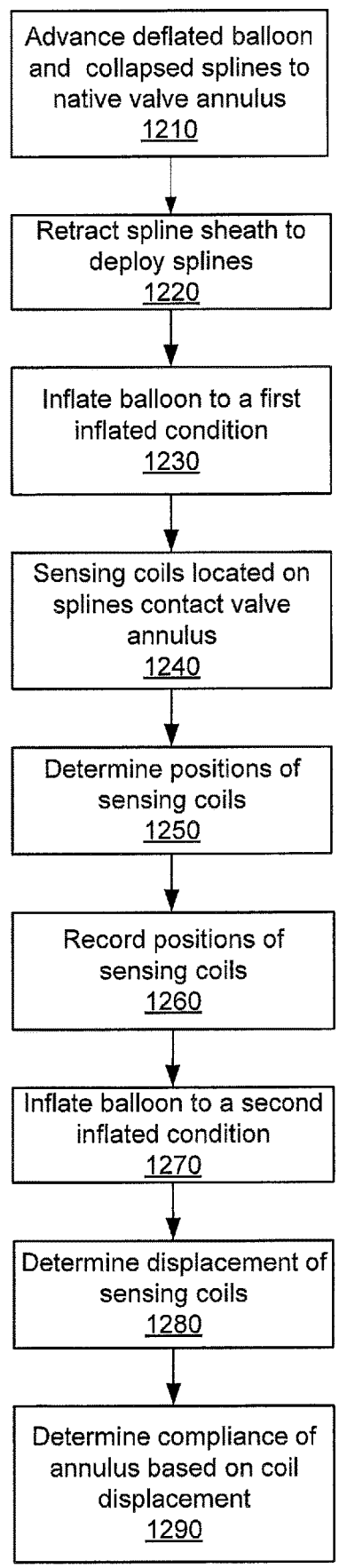
FIG. 12 is a flow chart depicting a method for determining the compliance of the valve annulus according to one aspect of the disclosure.

FIG. 12 is a flowchart depicting a method for determining the compliance, or lack thereof, of a native valve annulus using the sensing catheter depicted in FIGS. 11A and 11B. The method begins in block 1210 with the step of advancing the sensing balloon catheter over a guide wire to a native valve annulus. In this initial step, the catheter is advanced with the non- or semi-compliant balloon in the deflated state and the splines in the collapsed state. In block 1220, the spline sheath may be retracted in a known manner to deploy and expand the splines. In block 1230, the balloon may be inflated to a first inflated condition with a homogeneous medium (e.g., saline) until the balloon contacts the splines and, in block 1240, forces the sensing coils against the native valve annulus. The balloon may expand until it contacts and conforms to the native valve annulus.

In block 1250, the positions of the sensing coils are determined. In this regard, a magnetic tracking system, such as the Mediguide® system or the magnetic tracking system 4002 described above, may be used to determine the three-dimensional location of each of the sensing coils. In block 1260, the position of each of the sensing coils may be recorded. Recording the position of each sensing coil may include storing the position in memory, representing the position of each sensing coil graphically on a computing device, or a combination of both.

In block 1270, the balloon may be further inflated to a second inflated condition. In the second inflated condition, the balloon may exert a radial force on the valve annulus similar to the radial force exerted by the stent frame of a prosthetic heart valve. As the pressure in the balloon increases, the balloon may increase in diameter, compressing the native valve annulus in some locations more than in others. As the diameter of the balloon increases, the splines will be forced further outward until the sensing coils again contact the native valve annulus. In block 1280, the displacement of the sensing coils may be determined with sub-millimeter accuracy. In block 1290, the compliance of the annulus based on the displacement of the sensing coils is determined, which may be displayed graphically as discussed in greater detail above. The native valve annulus will have a relatively greater compliance where the displacement of the sensing coils is the greatest and a lesser compliance where the displacement of the sensing coils is less, thereby reflecting calcification. Thus, the method may detect varying degrees of calcification of the annulus based on the displacement of the sensing coils, which may be measured with sub-millimeter accuracy. Non-uniform calcification may lead to malapposition of a stent frame, which could cause paravalvular leakage.

Figure 13A:
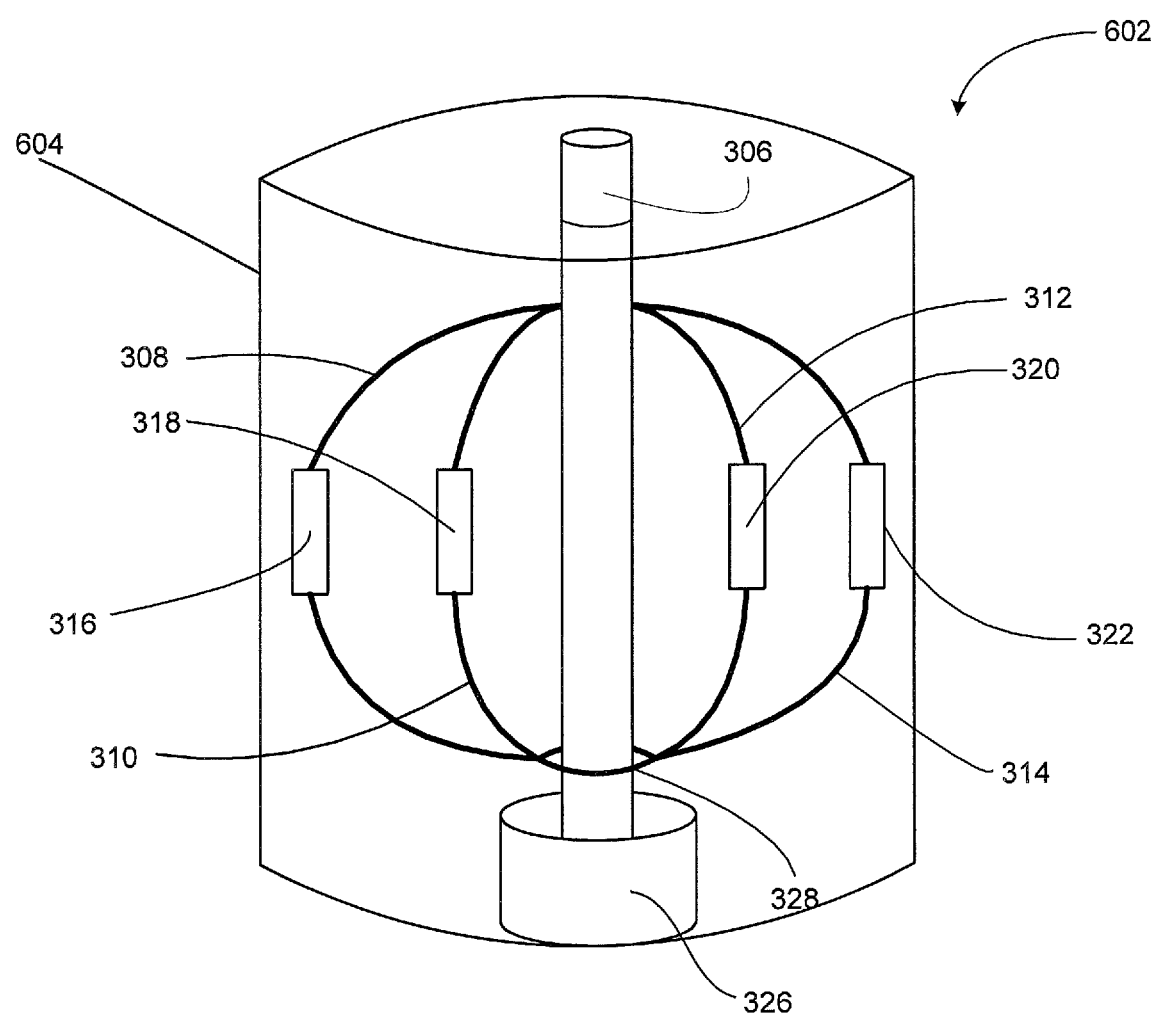
FIGS. 13A and 13B are schematic perspective views of a portion of a balloon catheter in which sensing coils are placed on splines extending from the shaft of the catheter according to another aspect of the disclosure.
Figure 13B:
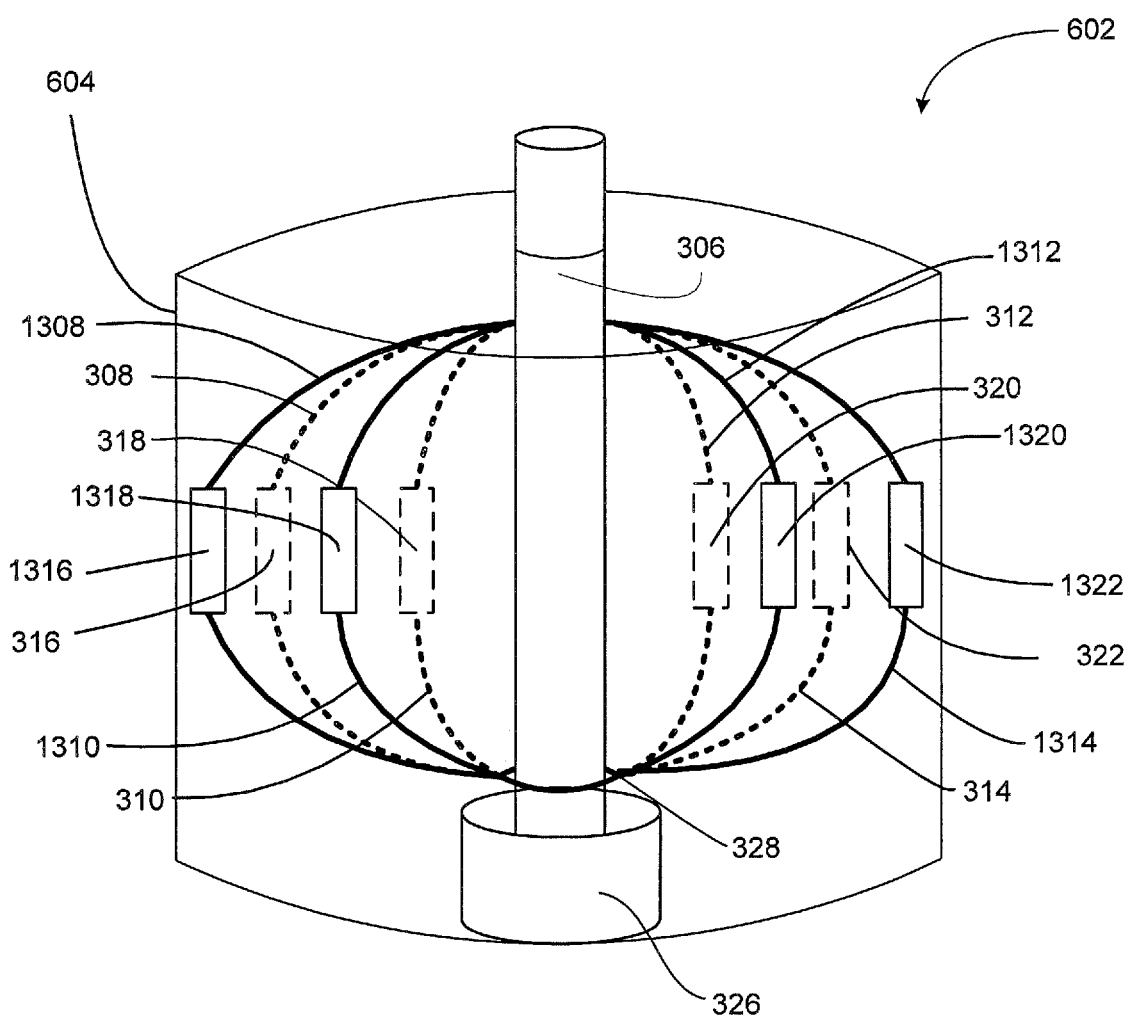

FIGS. 13A and 13B are schematic perspective views showing the use of sensing balloon catheter 602 described above (i.e., with splines 308, 310, 312 and 314 positioned within balloon 604) to determine the compliance of the native valve annulus. FIG. 13A shows the sensing balloon catheter 602 after non- or semi-compliant balloon 604 has been inflated to a first inflated condition and spline sheath 326 has been retracted. As described above, baseline locations of sensing coils 316, 318, 320, and 322 may be determined using the methods described above.

Turning to FIG. 13B, balloon catheter 602 is shown with balloon 604 at a greater pressure in a second inflated condition. In this regard, balloon 604 may exert a uniform pressure on the native valve annulus similar to the radial force that a stent frame would exert on the native valve annulus. Depending on which of the splines expand outwardly, one or more (or none) of sensing coils 316, 318, 320, and 322 may be displaced. For example, sensing coil 1316 shows the displacement of sensing coil 316 after balloon 604 has been further inflated. Similarly, sensing coil 1318 shows the displacement of sensing coil 318; sensing coil 1320 shows the displacement of sensing coil 320; and sensing coil 1322 shows the displacement of sensing coil 322.

Figure 14:
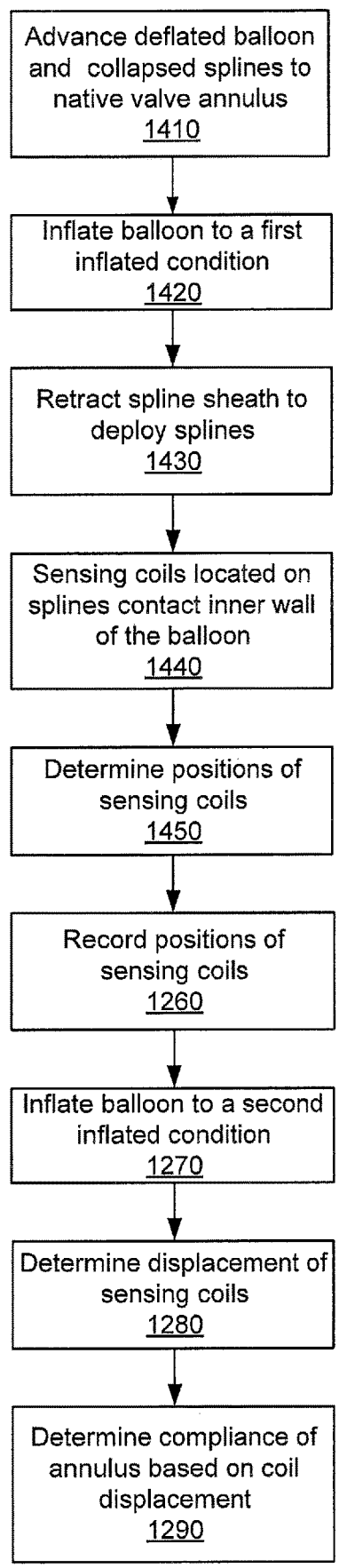
FIG. 14 is a flow chart depicting a method for determining the compliance of the valve annulus according to another aspect of the disclosure.

FIG. 14 illustrates a flow chart depicting a method for determining the compliance of a native valve annulus using the sensing catheter depicted in FIGS. 13A and 13B. The method begins in block 1410 by advancing the sensing balloon catheter over a guide wire to a native valve annulus. In block 1420, the non- or semi-compliant balloon may be inflated to a first inflated condition with a homogeneous medium. In block 1430, the spline sheath may be retracted in a known manner to deploy and expand the splines. In block 1440, the splines may expand outwardly until the sensing coils contact the inner wall of the inflated balloon. In block 1450, the positions of the sensing coils may be determined, and the position of each of the sensing coils may be recorded in block 1460. In block 1470, the balloon may be further inflated to a second inflated condition. In block 1480, the displacement of the sensing coils may be determined with sub-millimeter accuracy. Finally, the compliance of the annulus based on the displacement of the sensing coils is determined in block 1490.

Figure 15A:
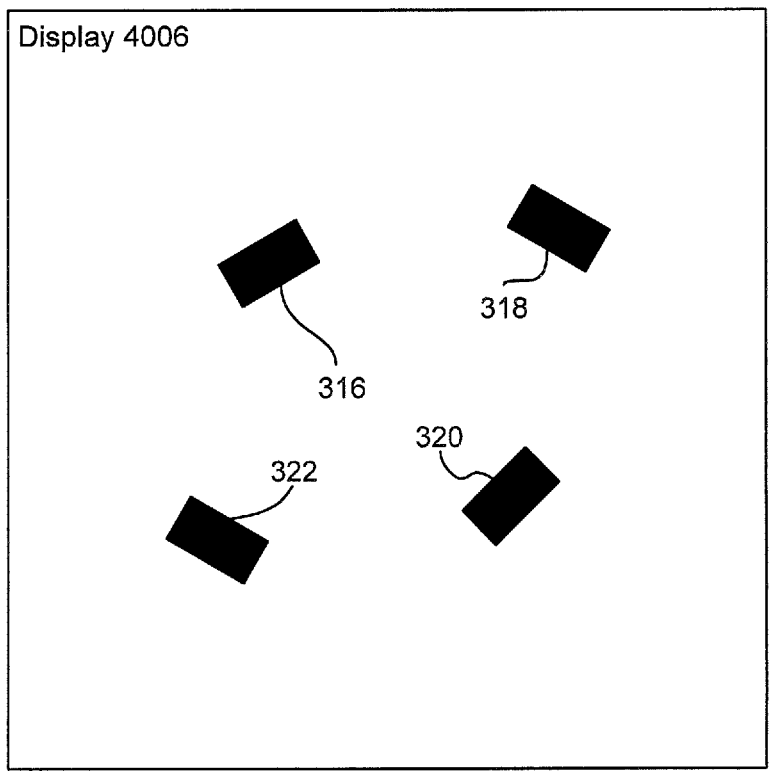
FIGS. 15A and 15B are diagrammatic views illustrating a display of the sensing coils according to one embodiment of the disclosure.
Figure 15B:
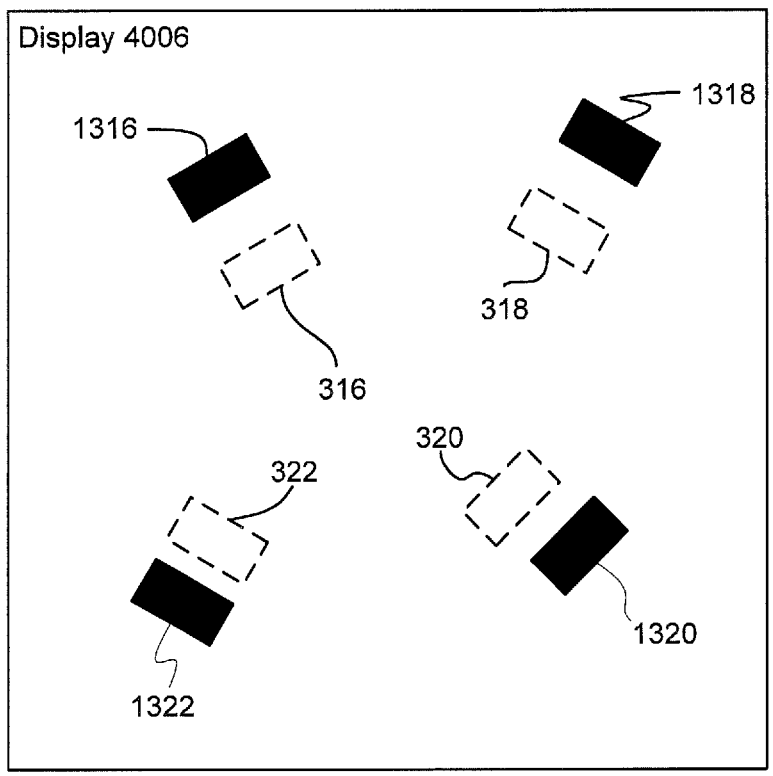

The displacement of the sensing coils with a small increase in pressure may be displayed graphically and measured with sub-millimeter accuracy. FIGS. 15A and 15B show an example in which the displacement of the coils is displayed. For example, FIG. 15A shows the baseline locations of sensing coils 316, 318, 320, and 322 on display 4006 after the initial deployment of the splines.

FIG. 15B shows the displacement of the sensing coils after the non- or semi-compliant balloon has been further inflated to the second inflation condition. Display 4006 may display the locations of the sensing coils shown in FIG. 15A in addition to the locations of the sensing coils following inflation of the balloon to the second inflated condition, as indicated by reference numerals 1316, 1318, 1320, and 1322. The sensing coils that travel a lesser distance may indicate a greater degree of calcification in that region of the native valve annulus since the native valve annulus would not deform as much in the second inflated condition in areas with greater degrees of calcification.

To summarize the foregoing, a system for determining the dimensions of a native valve annulus may include a sensing catheter having a shaft extending in a longitudinal direction; a plurality of splines attached to the shaft, the splines having an expanded condition spaced radially outward from the shaft; and at least one sensing coil located on each of the splines; a transmitter configured to generate a magnetic field to induce a potential in each of the sensing coils; and a computing device configured to identify positions of the sensing coils based on the induced potentials; and/or the sensing catheter may include an expandable balloon positioned between the shaft and the splines; and/or the transmitter may be an array of drive coils; and/or the system may include a display configured to output the position of each of the sensing coils; and/or the sensing catheter may include a ring slidably mounted on the shaft, each of the splines having one end attached to the shaft and another end attached to the ring; and/or the sensing catheter may include a spline sheath slidable relative to the shaft between a first position overlying the splines and a second position exposing the splines for movement to the expanded condition.

A method for determining the dimensions of a native valve annulus may include delivering a sensing catheter to a native valve annulus, the sensing catheter including a plurality of splines having a contracted condition and a radially expanded condition, each of the splines including a sensing coil; deploying the plurality of splines from the contracted condition to the radially expanded condition; generating at least one magnetic field that induces a potential in each of the sensing coils; determining a first position of each of the sensing coils based on the induced potentials; and determining a dimension of the native valve annulus based on the first positions of the sensing coils; and/or the deploying step may include deploying the plurality of splines so that the sensing coils are at a first plane relative to the native valve annulus; and/or the method may further include moving the plurality of splines from the radially expanded condition to the collapsed condition; rotating the sensing catheter to change the positions of the sensing coils; redeploying the plurality of splines from the contracted condition to the radially expanded condition so that the sensing coils are at the first plane relative to the native valve annulus; generating at least one magnetic field that induces a second potential in each of the sensing coils; determining a second position of each of the sensing coils based on the second induced potentials; and determining the dimension of the native valve annulus based on the first and second positions of the sensing coils; and/or the method may further include creating an image of the first plane of the native valve annulus by displaying first data points representing the first positions of the sensing coils and connecting each first data point with an adjacent first data point; and/or the creating step may include connecting each first data point with the adjacent first data point using a straight line or fitting a smooth curve to connect all of the first data points; and/or the method may further include moving the plurality of splines from the radially expanded condition to the collapsed condition; translating the sensing catheter so that the sensing coils are at a second plane different from the first plane relative to the native valve annulus; redeploying the plurality of splines from the contracted condition to the radially expanded condition so that the sensing coils are at the second plane relative to the native valve annulus; generating at least one magnetic field that induces a second potential in each of the sensing coils; determining a second position of each of the sensing coils based on the second induced potentials; and determining a second dimension of the native valve annulus based on the second positions of the sensing coils; and/or the method may further include creating an image of the second plane of the native valve annulus by displaying second data points representing the second positions of the sensing coils and connecting each second data point with an adjacent second data point; and/or the method may further include constructing a three-dimensional model of the native valve annulus based on the image of the first plane of the native valve annulus and the image of the second plane of the native valve annulus; and/or the sensing catheter may include a shaft and a balloon positioned between the splines and the shaft, and the deploying step may include inflating the balloon to a first inflated condition between the deploying step and the generating step; and/or the method may further include inflating the balloon to a second inflated condition after the determining step; and/or the method may further include, after the step of inflating the balloon to the second inflated catheter, generating at least one magnetic field that induces a second potential in each of the sensing coils; determining a second position of each of the sensing coils based on the second induced potentials; determining a displacement of each of the sensing coils based on the first and second positions; and determining a degree of compliance of the native valve annulus based on the displacement of each of the sensing coils; and/or the displacement of each of the sensing coils may be the difference between the second position of the sensing coil and the first position of the sensing coil; and/or the method may further include determining a degree of calcification of the native valve annulus based on the degree of compliance.

An apparatus may include a shaft extending in a longitudinal direction; a plurality of splines attached to the shaft, the splines having an expanded condition spaced radially outward from the shaft; at least one sensing coil located on each of the splines; and an expandable balloon positioned between the shaft and the splines.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A system for determining the dimensions of a native valve annulus, the system comprising:
   a sensing catheter that includes:
      a shaft extending in a longitudinal direction;
      a plurality of splines positioned about the shaft, each spline having a first end fixedly attached to the shaft and a second end, the splines having an unconstrained expanded condition spaced radially outward from the shaft, the splines in the unconstrained expanded condition collectively defining a plurality of circles that are perpendicular to the longitudinal direction;
      a ring slidably mounted around the shaft, the second end of each of the splines being attached to the ring; and
      each of the splines including a sensing coil located at an expansion center of the spline, the expansion center being a position on the spline such that the expansion centers of the plurality of splines collectively define a largest one of the plurality of circles;
   a transmitter configured to generate a magnetic field to induce a potential in each of the sensing coils; and
   a computing device configured to identify positions of the sensing coils based on the induced potentials.

2. The system of claim 1, wherein the sensing catheter includes an expandable balloon positioned between the shaft and the splines.

3. The system of claim 1, wherein the transmitter is an array of drive coils.

4. The system of claim 1, further comprising:
   a display configured to output the position of each of the sensing coils.

5. The system of claim 1, wherein the sensing catheter further comprises:
   a spline sheath slidable relative to the shaft between a first position overlying the splines and a second position exposing the splines for movement toward the expanded condition.

6. A method for determining the dimensions of a native valve annulus, the method comprising:
   delivering a sensing catheter to a native valve annulus, the sensing catheter including a shaft extending in a longitudinal direction and a plurality of splines, each spline having a first end fixedly attached to the shaft and a second end, the splines having a contracted condition and an unconstrained radially expanded condition, the splines in the unconstrained expanded condition collectively defining a plurality of circles that are perpendicular to the longitudinal direction, each of the splines including a sensing coil located at an expansion center of the spline, the expansion center being a position on the spline such that the expansion centers of the plurality of splines collectively define a largest one of the plurality of circles;
   deploying the plurality of splines from the contracted condition to a second radially expanded condition in which ones of the sensing coils contact the native valve annulus and each of the sensing coils lies in a first plane relative to the native valve annulus;
   generating at least one magnetic field that induces a first potential in each of the sensing coils;
   determining a first position of each of the sensing coils based on the first induced potentials;
   moving the plurality of splines from the second radially expanded condition to the contracted condition;
   rotating the sensing catheter to change the positions of the sensing coils;
   redeploying the plurality of splines from the contracted condition to a third radially expanded condition in which ones of the sensing coils contact the native valve annulus and each of the sensing coils lies in the first plane relative to the native valve annulus;
   generating at least one magnetic field that induces a second potential in each of the sensing coils;
   determining a second position of each of the sensing coils based on the second induced potentials; and
   determining a dimension of the native valve annulus based on the first and second positions of the sensing coils.

7. The method of claim 6, further comprising:
   creating an image of a first plane of the native valve annulus by displaying first data points representing the first positions of the sensing coils and connecting each first data point with an adjacent first data point.

8. The method of claim 7, wherein the creating step includes connecting each first data point with the adjacent first data point using a straight line or fitting a smooth curve to connect all of the first data points.

9. The method of claim 6, wherein the sensing catheter includes a balloon positioned between the splines and the shaft, the method further comprising:
   inflating the balloon to a first inflated condition between the deploying step and the step of generating at least one magnetic field that induces the first potential in each of the sensing coils.

10. A method for determining the dimensions of a native valve annulus, the method comprising:
   delivering a sensing catheter to a native valve annulus, the sensing catheter including a shaft extending in a longitudinal direction and a plurality of splines, each spline having a first end fixedly attached to the shaft and a second end, the splines having a contracted condition and an unconstrained radially expanded condition, the splines in the unconstrained expanded condition collectively defining a plurality of circles that are perpendicular to the longitudinal direction, each of the splines including a sensing coil located at an expansion center of the spline, the expansion center being a position on the spline such that the expansion centers of the plurality of splines collectively define a largest one of the plurality of circles;
   deploying the plurality of splines from the contracted condition to a second radially expanded condition in which ones of the sensing coils contact the native valve annulus and each of the sensing coils lies in a first plane relative to the native valve annulus;
   generating at least one magnetic field that induces a first potential in each of the sensing coils;
   determining a first position of each of the sensing coils based on the first induced potentials;
   determining a first dimension of the native valve annulus based on the first positions of the sensing coils;
   moving the plurality of splines from the second radially expanded condition to the contracted condition;
   translating the sensing catheter so that the sensing coils are at a second plane different from the first plane relative to the native valve annulus;

redeploying the plurality of splines from the contracted condition to a third radially expanded condition in which ones of the sensing coils contact the native valve annulus and each of the sensing coils lies in the second plane relative to the native valve annulus;

generating at least one magnetic field that induces a second potential in each of the sensing coils;

determining a second position of each of the sensing coils based on the second induced potentials; and determining a second dimension of the native valve annulus based on the second positions of the sensing coils.

11. A system for determining the dimensions of a native valve annulus, the system comprising:

a sensing catheter that includes:

a shaft extending in a longitudinal direction;

a plurality of splines positioned about the shaft, each spline having a first end fixedly attached to the shaft and a second end, the splines having an unconstrained expanded condition spaced radially outward from the shaft;

a ring slidably mounted around the shaft, the second end of each of the splines being attached to the ring; and each of the splines including a sensing coil located between the first end and the second end of the spline and at a position spaced from both the first end and the second end of the spline, the position being at an expansion center of the spline when the spline is in the unconstrained expanded condition;

a transmitter configured to generate a magnetic field to induce a potential in each of the sensing coils; and a computing device configured to identify positions of the sensing coils based on the induced potentials.

12. The method of claim 10, further comprising:

creating an image of a first plane of the native valve annulus by displaying first data points representing the first positions of the sensing coils and connecting each first data point with an adjacent first data point.

13. The method of claim 12, further comprising:

creating an image of a second plane of the native valve annulus by displaying second data points representing the second positions of the sensing coils and connecting each second data point with an adjacent second data point.

14. The method of claim 13, further comprising:

constructing a three-dimensional model of the native valve annulus based on the image of the first plane of the native valve annulus and the image of the second plane of the native valve annulus.

* * * * *